United States Patent
Tanzi et al.

(12)

(10) Patent No.: US 6,365,414 B1
(45) Date of Patent: Apr. 2, 2002

(54) VITRO SYSTEM FOR DETERMINING FORMATION OF Aβ AMYLOID

(75) Inventors: Rudolph E. Tanzi, Canton; Ashley I. Bush, Boston, both of MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 08/294,819

(22) Filed: Aug. 26, 1994

(51) Int. Cl.$^7$ .......................... G01N 21/75; G01N 33/50
(52) U.S. Cl. ........................ 436/86; 436/164; 436/177; 436/811
(58) Field of Search .......................... 436/86, 164, 177, 436/811

(56) References Cited

U.S. PATENT DOCUMENTS

| | | | |
|---|---|---|---|
| 4,666,829 A | | 5/1987 | Glenner et al. ................. 435/6 |
| 5,164,295 A | * | 11/1992 | Kisilevsky et al. ........... 435/7.8 |
| 5,231,000 A | | 7/1993 | Majocha et al. .............. 435/7.1 |
| 5,242,932 A | | 9/1993 | Gandy et al. ................ 514/313 |
| 5,262,332 A | | 11/1993 | Selkoe ........................ 436/518 |
| 5,276,059 A | | 1/1994 | Caughey et al. ............. 514/647 |
| 5,434,050 A | * | 7/1995 | Maggio et al. ............. 435/7.21 |

FOREIGN PATENT DOCUMENTS

| WO | WO 94/17197 | 8/1994 |
|---|---|---|

OTHER PUBLICATIONS

Fitzgerald, D.J., Maggio, J.E. et al., and Bush, A.I. et al., "Technical Comments: Zinc and Alzheimer's Disease", *Science* 268:1920–1923 (Jun. 30, 1995).
Kim et al., "Detection and Quantitation of Amyloid B–Peptide with 2 Monoclonal Antibodies," *Neurosci. Res. Comm.* 7(2):113–122 (1990).
Suzuki et al., "High Tissue Content of Soluble β1–40 is Linked to Cerebral Amyloid Angiopathy," *Amer. J. Pathology* 145(2):452–460 (1994).
Assaf and Chung, "Release of endogenous $Zn^{2+}$ from brain tissue during activity," *Nature* 308:734–736 (1984).
Backstrom et al., "Characterization of Neutral Proteinases from Alzheimer–Affected and Control Brain Specimens: Identification of Calcium–Dependent Metalloproteinases from the Hippocampus," *J. Neurochem.* 58(3):983–992 (1992).
Baker et al., "Platelet Metal Levels in Normal Subjects Determined by Atomic Absorption Spectrophotometry," *Thrombos. Haemostas.* 39:360–365 (1978).
Björkstén et al., "Zinc and Immune Function in Down's Syndrome," *Acta Pædiatr. Scand.* 69:183–187 (1980).
Bush et al., "An Abnormality of Plasma Amyloid Protein Precursor in Alzheimer's Disease," *Ann. Neurol.* 32:57–65 (1992).

Bush et al., "The Amyloid Precursor Protein of Alzheimer's Disease Is Released by Human Platelets," *J. Biol. Chem.* 265(26):15977–15983 (1990).
Bush et al., "Modulation of Aβ Adhesiveness and Secretase Site Cleavage by Zinc," *J. Biol. Chem.* 269(16):12152–12158 (1994).
Bush et al., "A Novel Zinc (II) Binding Site Modulates the Function of the βA4 Amyloid Protein Precursor of Alzheimer's Disease," *J. Biol. Chem.* 268(22):16109–16112 (1993).
Candy et al., "Aluminosilicates and Senile Plaque Formation in Alzheimer's Disease," *Lancet:*354–357 (Feb. 15, 1986).
Candy et al., "Amorphous aluminosilicates promote nucleation of amyloid β protein and tachykinins," *Biochem. Soc. Trans.* 21:53S (Abstract) (1992).
Constantinidis, J., "Maladie d'Alzheimer et la théorie du zinc," *L'Encéphale XVI:*231–239 (1990).
Corrigan et al., "Hippocampal tin, aluminum and zinc in Alzheimer's Disease," *Biometals* 6:149–154 (1993).
Crapper McLachlan et al., "Intramuscular desferrioxamine in patients with Alzheimer's disease," *Lancet* 337:1304–1308 (1991).
Davies et al., "Measurements of plasma zinc," *J. Clin. Path.* 21:359–365 (1968).
Duncan et al., "Zinc, a Neurotoxin to Cultured Neurons, Contaminates Cycad Flour Prepared by Traditional Guamanian Methods," *J. Neurosci.* 12(4):1523–1537 (1992).
Esch et al., "Cleavage of Amyloid β Peptide During Constitutive Processing of Its Precursor," *Science* 248:1122–1124 (1990).
Folstein et al., "Mini–Mental State," *J. Psychiatr. Res.* 12:189–198 (1975).
Franceschi et al., "Oral zinc supplementation in Down's syndrome: restoration of thymic endocrine activity and of some immune defects," *J. Ment. Defic. Res.* 32:169–181 (1988).

(List continued on next page.)

*Primary Examiner*—Jan Ludlow
(74) *Attorney, Agent, or Firm*—Sterne, Kessler, Goldstein & Fox

(57) ABSTRACT

The invention relates to rapid methods for determining formation of Aβ amyloid and screening compounds which inhibit formation of Aβ amyloid in vitro, as well as kits for carrying out the present methods. Such an agent used in vivo may prevent, ameliorate or reverse the symptoms of Alzheimer's disease and Aβ amyloidotic disorders related to Alzheimer's disease, Down's syndrome, and Guamanian amyotrophic lateral sclerosis/Parkinson's dementia complex. The process described in this invention involves the rapid induction of Aβ amyloid by a heavy metal cation capable of binding to a polypeptide comprising at least amino acids 6 to 28 of Aβ, such as zinc to form amyloid and determination of formation of tinctorial Aβ amyloid. Moreover, a method of determining effectiveness of a candidate anti-amyloidotic agent for prevention or treatment of Aβ amyloidosis is described which uses cell cultures which express at least a human Aβ peptide.

4 Claims, 25 Drawing Sheets

OTHER PUBLICATIONS

Frederickson, C.J., "Neurobiology of Zinc and Zinc–Containing Neurons," *Int. Rev. Neurobiol.* 31:145–238 (1989).

Frederickson et al., "Cytoarchitectonic Distribution of Zinc in the Hippocampus of Man and the Rat," *Brain Res.* 273:335–339 (1983).

Frederickson et al., "Zinc–containing 7S–NGF Complex. Evidence From Zinc Histochemistry for Localization in Salivary Secretory Granules," *J. Histochem. Cytochem.* 35(5):579–583 (1987).

Fredericq, E., "The Association of Insulin Molecular Units in Aqueous Solutions," *Arch. Biochem. Biophys.* 65:218–228 (1956).

Galasko et al., "Monitoring Progression in Alzheimer's Disease," *JAGS* 39:932–941 (1991).

Garruto et al., "Imaging of calcium and aluminum in neurofibrillary tangle–bearing neurons in parkinsonism–dementia of Guam," *PNAS USA* 81:1875–1879 (1984).

Glenner and Wong, "Alzheimer's disease: initial report of the purification and characterization of a novel cerebrovascular amyloid protein," *Biochem. Biophys. Res. Commun.* 120:885–890 (1984).

Guiroy et al., "Amyloid of neurofibrillary tangles of Guamanian parkinsonism–dementia and Alzheimer disease share identical amino acid sequence," *PNAS USA* 84:2073–2077 (1987).

Haass et al., "Amyloid β–peptide is produced by cultured cells during normal metabolism," *Nature* 359:322–325 (1992).

Hershey et al., "Cerebrospinal fluid trace element content in dementia: Clinical, radiologic, and pathologic correlation," *Neurology* 33:1350–1353 (1983).

Hilbich et al., "Aggregation and Secondary Structure of Synthetic Amyloid βA4 Peptides of Alzheimer's Disease," *J. Mol. Biol.* 218:149–163 (1991).

Howell et al., "Stimulation–induced uptake and release of zinc in hippocampal slices," *Nature* 308:736–738 (1984).

Hyman et al., "Perforant Pathway Changes and the Memory Impairment of Alzheimer's Disease," *Ann. Neurol.* 20(4):472–481 (1986).

Jarrett et al., "The Carboxy Terminus of the β Amyloid Protein is Critical for the Seeding of Amyloid Formation: Disease," *Biochem.* 32(18):4693–4697 (1993).

Johnstone et al., "Conservation of the sequence of the Alzheimer's disease amyloid peptide in dog, polar bear and five other mammals by cross–species polymerase chain reaction analysis," *Mol. Brain Res.* 10:299–305 (1991).

Koh et al., "β–Amyloid protein increases the vulnerability of cultured cortical neurons to excitotoxic damage," *Brain Res.* 533:315–320 (1990).

Koo et al., "Amyloid β–protein as a substrate interacts with extracellular matrix to promote neurite outgrowth," *PNAS USA* 90:4748–4752 (1993).

Lui et al., "Metals and the Liver in Alzheimer's Disease. An Investigation of Hepatic Zinc, Copper, Cadmium, and Metallothionein," *JAGS* 38:633–639 (1990).

Mantyh et al., "Aluminum, Iron, and Zinc Ions Promote Aggregation of Physiological Concentrations of β–Amyloid Peptide," *J. Neurochem.* 61(3):1171–1174 (1993).

Masters et al., "Amyloid plaque core protein in Alzheimer disease and Down syndrome," *PNAS USA* 82:4245 (1985).

Masters et al., "Neuronal origin of a cerebral amyloid: neurofibrillary tangles of Alzheimer's disease contain the same protein as the amyloid of plaque cores and blood vessels," *EMBO J.* 4(11):2757–2763 (1985).

Milward et al., "The Amyloid Protein Precursor of Alzheimer's Disease Is a Mediator of the Effects of Nerve Growth Factor on Neurite Outgrowth," *Neuron* 9:129–137 (1992).

Pérez–Clausell and Danscher, "Intravesicular Localization of Zinc in Rat Telencephalic Boutons. A Histochemical Study," *Brain Res.* 337:91–98 (1985).

Perl and Brody, "Alzheimer's Disease: X–ray Spectrometric Evidence of Aluminum Accumulation in Neurofibrillary Tangle–Bearing Neurons," *Science* 208:297–299 (1980).

Perl et al., "Intraneuronal Aluminum Accumulation in Amyotrophic Lateral Sclerosis and Parkinsonism–Dementia of Guam," *Science* 217:1053–1055 (1982).

Rumble et al., "Amyloid A4 Protein and its Precursor in Down's Syndrome and Alzheimer's Disease," *New Eng. J. Med.* 320(22):1446–1452 (1989).

Schubert et al., "Localization of Alzheimer βA4 amyloid precursor protein at central and peripheral synaptic sites," *Brain Res.* 563:184–194 (1991).

Seubert et al., "Isolation and quantification of soluble Alzheimer's β–peptide from biological fluids," *Nature* 359:325–327 (1992).

Shivers et al., "Alzheimer's disease amyloidogenic glycoprotein: expression pattern in rat brain suggests a role in cell contact," *EMBO J.* 7(5):1365–1370 (1988).

Shoji et al., "Production of the Alzheimer Amyloid β Protein by Normal Proteolytic Processing," *Science* 258:126–129 (1992).

Sisodia et al., "Evidence That β–Amylid Protein in Alzheimer's Disease Is Not Derived by Normal Processing," *Science* 248:492–495 (1990).

Stewart et al., "Cholinergic Denervation–Induced Increase of Chelatable Zinc in Mossy–Fiber Region of the Hippocampal Formation," *Brain Res.* 290:43–51 (1984).

Tomski and Murphy, "Kinetics of Aggregation of Synthetic β–Amyloid Peptide," *Arch. Biochem. Biophys.* 294(2):630–638 (1992).

Uchida et al., "The Growth Inhibitory Factor That Is Deficient in the Alzheimer's Disease Brain is a 68 Amino Acid Metallothionein–like Protein," *Neuron* 7:337–347 (1991).

Vaughan and Peters, "The Structure of Neuritic Plaques in the Cerebral Cortex of Aged Rats," *J. Neuropathol. Exp. Neurol.* 40(4):472–487 (1981).

Weiss et al., "Zinc and LTP," *Nature* 338:212 (1989).

Wenstrup et al., "Trace element imbalances in isolated subcellular fractions of Alzheimer's disease brains," *Brain Res.* 533:125–131 (1990).

Wolf et al., "Uptake and Subcellular Distribution of $^{65}$Zinc in Brain Structures During the Postnatal Development of the Rat," *Neurosci. Lett.* 51:277–280 (1984).

Xie and Smart, "A physiological role for endogenous zinc in rat hippocampal synaptic neurotransmission," *Nature* 349:521–524 (1991).

Yanker et al., "Neurotrophic and Neurotoxic Effect of Amyloid β Protein: Reversal by Tachykinin Neuropeptides," *Science* 250:279–282 (1990).

\* cited by examiner

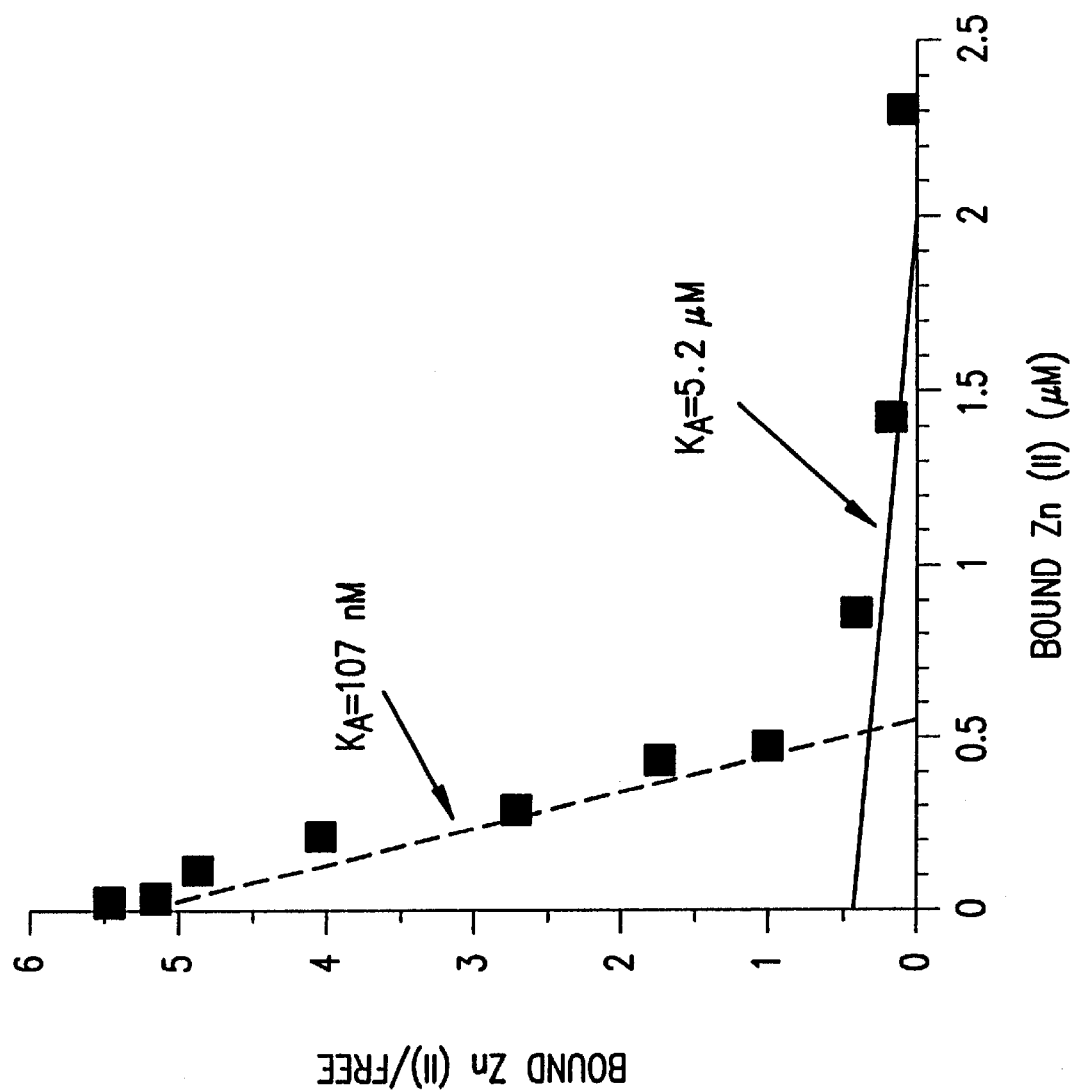

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
       (A) LENGTH: 43 amino acids
       (B) TYPE: amino acid
       (C) STRANDEDNESS: unknown
       (D) TOPOLOGY: unknown (xi) SEQUENCE DESCRIPTION: SEQ ID NO:1:

```
Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala Thr
            35                  40
```

VITRO SYSTEM FOR DETERMINING FORMATION OF Aβ AMYLOID

STATEMENT AS TO RIGHTS TO INVENTIONS MADE UNDER FEDERALLY-SPONSORED RESEARCH AND DEVELOPMENT

Part of the work performed during the development of this invention utilized U.S. Government Funds under Grants Nos. RO1 NS3048-03 and RO1 AG11899-01 from The National Institutes of Health (NIH). The government may have certain rights in this invention.

BACKGROUND OF THE INVENTION

1. Field of the Invention

The present invention is directed to various assays for detection of Aβ amyloid, screening candidate agents for their ability to prevent or reverse the formation of Aβ amyloid in vitro, as well as kits which are used in the present methods.

2. Related Art

Aggregation of Aβ in the brain is believed to contribute to dementia, characteristic of Alzheimer's disease (AD) and Down's syndrome, a condition characterized by premature AD. Aβ, a 4.3-kDa peptide, is the principal constituent of the cerebral amyloid deposits, a pathological hallmark of Alzheimer's disease (AD) (Masters et al., *Proc. Natl. Acad. Sci. USA* 82:4245–4249 (1985); Glenner & Wong, *Biochem. Biophys. Rev. Commun.* 120:885–890 (1984)). Aβ is derived from the much larger amyloid protein precursor (APP) (Kang et al., *Nature* 325:733–736 (1987); Tanzi et al., *Science* 235:880–884 (1987); Robakis et al., *Proc. Natl. Acad. Sci. USA* 84:4190–4194 (1987); Goldgaber et al., *Science* 235:877–880 (1987)), whose physiological function remains unclear. The cause of Alzheimer's disease remains elusive; however, the discovery of mutations of APP close to or within the Aβ domain (Goate et al., *Nature* 349:704–706 (1991); Levy et al., *Science* 248:1124–1126 (1990); Murrell et al., *Science* 254:97–99 (1991); Hendricks et al., *Nature Genet.* 1:218–221 (1992), linked to familial AD (E. Levy et al., *Science* 248:1124 (1990); Aβ Goate et al., *Nature* 349:704 (1991); M. Chartier-Harlin et al., *Nature* 353:844 (1991); J. Murrell, M. Farlow, B. Ghetti, M. D. Benson, *Science* 254:97 (1991); L. Hendricks et al., *Nature Genet.* 1:218 (1992); M. Mullan et al., *Nature Genet.* 1:345 (1992)), indicates that the metabolism of Aβ and APP is likely to be intimately involved with the pathophysiology of this disorder.

Soluble Aβ is secreted in cell cultures and is found as a 40-residue peptide ($A\beta_{1-40}$) in the cerebrospinal fluid (CSF) (Shoji et al., *Science* 258 126–129 (1992); Seubert et al., *Nature* 359:325–327 (1992); Haass et al., *Nature* 359:322–325 (1992)), but is not found at elevated levels in sporadic AD cases (M. Shoji et al., *Science* 258:126 (1992); P. Seubert et al., *Nature* 359:325 (1992)). Physiological factors which can induce the aggregation of soluble Aβ are of interest in determining the cause of Aβ amyloid formation. Synthetic $A\beta_{1-40}$ remains soluble at concentrations up to 16 mg/ml in neutral phosphate buffer (Tomski & Murphy, *Arch. Biochem. Biophys.* 294:630–638 (1992)), indicating that overproduction of soluble Aβ cannot sufficiently explain Aβ precipitation. Hence, biochemical mechanisms which promote Aβ amyloid formation in sporadic cases would appear to be relevant to the pathogenesis of AD. Furthermore, soluble Aβ in cerebrospinal fluid is not increased in AD cases (Shoji et al., *Science* 258: 126–129 (1992)), indicating that other pathogenetic mechanisms are likely to be involved.

In recent years, the study of Aβ peptide has led to making cell lines that express or overexpress Aβ or its precursor protein, APP or increased amounts of its more amyloidogenic $A\beta_{1-42}$ form. See N. Suzuki et al., *Science* 264:1336–1340 (1994); X-D Cai et al., *Science* 259:514–516 (1993); F. S. Esch et al., *Science* 248:1122–1124 (1990). Moreover, monoclonal antibodies to Aβ peptide have been generated (see, e.g. U.S. patent Ser. No. 5,231,000, issued Jul. 27, 1993). These monoclonal antibodies are useful as reagents for use in detecting presence of Aβ amyloid.

SUMMARY OF THE INVENTION

The process described in this invention involves the rapid induction of Aβ amyloid by a heavy metal cation such as zinc to form amyloid. In a preferred embodiment of the invention, the proportion of an $A\beta_{1-40}$ solution which remains filtrable after incubation with zinc is assayed and the effects of candidate pharmacological agents on the filtrate are measured to determine their ability to maintain the solubility of Aβ in physiological solution and thus prevent Aβ amyloid formation.

A method for the in vitro induction of Aβ amyloid has been previously described (J. T. Jarrett et al., *Biochem.* 32:4693–4697 (1993)). However, this method has many disadvantages, such as a requirement for high concentrations of peptide and prolonged incubation periods (days) with results that are qualitative rather than quantitative. In contrast, some of the major advantages of the present invention are that the technique is reliable, rapid (can be carried out in minutes), is easily quantifiable, and is achieved with low micromolar concentrations of peptide.

Hence, the present invention relates to an in vitro method for the rapid screening of candidate reagents which are likely to be effective in preventing or reversing the formation of amyloid deposits in vivo which are characteristic of Alzheimer's disease and related pathological conditions. Promising candidate reagents which are selected through one of the in vitro methods of the present invention may then be tested for their effectiveness in vivo in patients which are suffering from Alzheimer's disease or who are at risk for developing Alzheimer's disease.

One aspect of the invention relates to a rapid analytical method for detection of Aβ amyloid formation in a biological fluid which comprises:

(a) preparing a first set of reaction mixtures comprising neat biological fluid from a control human subject, and serial dilutions of the same made in aqueous buffer or physiological solution;

(b) preparing a second set of reaction mixtures comprising neat biological fluid from a human patient suspected of amyloidosis, and serial dilutions of the same made in aqueous buffer or physiological solution;

(c) adding an equal amount of AB peptide comprising at least amino acids 6 to 28 of Aβ to each serial dilution sample;

(d) contacting each of the first and the second set of reaction mixtures with an amount greater than 300 nM of a heavy metal cation capable of binding to an Aβ peptide comprising at least amino acids 6 to 28 of Aβ;

(e) centrifuging each of the first and the second sets of reaction mixtures to give a first and a second set of pellets, respectively; and (f) comparing the amount of amyloid in the first and the second set of pellets and thereby detecting excessive Aβ amyloid formation in the biological fluid from the human patient suspected of amyloidosis.

A second aspect of the invention relates to a method for determining whether a compound inhibits the formation of Aβ amyloid which comprises:

(a) pre-filtering an aqueous buffer solution of Aβ peptide, which comprises at least the region in the Aβ peptide from amino acid number 6 to 28 to give a first filtrate;

(b) measuring the amount of Aβ peptide in the first filtrate obtained in step (a);

(c) contacting the first filtrate obtained in step (a) with a heavy metal cation capable of binding to the peptide comprising at least amino acids 6 to 28 of Aβ to give a reaction mixture;

(d) contacting the reaction mixture obtained in step (c) with a candidate anti-amyloidotic agent;

(e) filtering the reaction mixture obtained in step (d) to give a second filtrate; and (f) comparing the amount of Aβ peptide in the second filtrate with the amount of Aβ peptide in the first filtrate, thereby determining whether the candidate compound inhibits formation of Aβ amyloid.

A third aspect of the invention relates to a method for determining whether a compound inhibits formation of Aβ amyloid which comprises:

(a) assembling a first and a second reaction mixture, wherein each reaction mixture comprises an equal amount of a pre-filtered Aβ peptide solution, which comprises at least the region in the Aβ peptide from amino acid number 6 to 28, and an aqueous buffer or physiological solution;

(b) contacting each of the first and the second reaction mixtures with an equal amount of a candidate anti-amyloidotic agent;

(c) contacting the first reaction mixture with a heavy metal cation capable of binding to the peptide comprising at least amino acids 6 to 28 of Aβ;

(d) contacting the second reaction mixture with EDTA; and (e) comparing the amount of amyloid formed in the first reaction mixture with that in the second reaction mixture, thereby determining whether the candidate compound inhibits the formation of Aβ amyloid.

A fourth aspect of the invention relates to a method for determining whether a compound inhibits formation of Aβ amyloid which comprises:

(a) assembling a first and a second reaction mixture, wherein each reaction mixture comprises an equal amount of a prefiltered Aβ peptide solution, which contains at least the region in the Aβ peptide from amino acid number 6 to 28, and an aqueous buffer or physiological solution;

(b) contacting each of the first and the second reaction mixtures with an equal amount of a candidate anti-amyloidotic agent;

(c) contacting only the first reaction mixture with a heavy metal cation capable of binding to the peptide comprising at least amino acids 6 to 28 of Aβ; and (d) comparing the amount of amyloid formed in the first reaction mixture with that in the second reaction mixture, thereby determining whether the compound inhibits formation of Aβ amyloid.

A fifth aspect of the invention relates to a method for determining whether a compound inhibits formation of Aβ amyloid which comprises:

(a) establishing a first and a second cell culture comprising a cell line which expresses at least a human Aβ peptide comprising at least the region of the Aβ peptide from amino acid number 6 to 28;

(b) contacting equal concentrations of zinc to each cell culture;

(c) contacting the first cell culture with the candidate agent, and contacting the second cell culture with a heavy metal chelatating agent; and (d) comparing the amount of amyloid and zinc-induced Aβ aggregates in each cell culture, thereby determining effectiveness of the candidate anti-amyloidotic agent.

A sixth aspect of the invention relates to a method for determining whether a compound inhibits formation of Aβ amyloid which comprises:

(a) establishing a first and a second cell culture comprising a cell line which expresses at least a human Aβ peptide comprising at least the region of the Aβ peptide from amino acid number 6 to 28;

(b) contacting the first cell culture with zinc to give a first reaction mixture;

(c) contacting the first reaction mixture and the second cell culture with the candidate agent; and (d) comparing the amount of amyloid and zinc-induced Aβ aggregates in each cell culture, thereby determining effectiveness of the candidate anti-amyloidotic agent.

A seventh aspect of the invention relates to a kit for determining whether a compound inhibits formation of Aβ amyloid which comprises a carrier means being compartmentalized to receive in close confinement therein one or more container means wherein (a) the first container means contains a peptide comprising at least the region of the Aβ peptide from amino acid number 6 to 28; and (b) a second container means contains a heavy metal cation.

BRIEF DESCRIPTION OF THE FIGURES

FIGS. 1a, 1b, 1c, 1d and 1e. Analyses of $^{65}Zn^{2+}$ binding to Aβ. Values shown are means±S.D., n≧3. (1a) Scatchard plot. Aliquots of Aβ were incubated (60 min) with $^{65}Zn^{2+}$ in the presence of varying concentrations of unlabeled $Zn^{2+}$ (0.01–50 μM total). The proportion of $^{65}Zn^{2+}$ binding to immobilized peptide (1.0 nmol) described two binding curves as shown. The high-affinity binding curve has been corrected by subtracting the low-affinity component, and the low-affinity curve has had the high-affinity component subtracted. (1b) Bar graph showing the specificity of the $Zn^{2+}$ binding site for metals. Aβ was incubated (60 min) with $^{65}Zn^{2+}$ (157 nM, 138,000 cpm) and competing unlabeled metal ions (50 μM total). (1c) Bar graph showing $^{65}Zn^{2+}$ (74 nM, 104,000 cpm) binding to negative (aprotinin, insulin a-chain, reverse peptide 40-1) and positive (bovine serum albumin (BSA)) control proteins and Aβ fragments (identified by their residue numbers within the Aβ sequence, gln11 refers to $Aβ_{1-28}$ where residue 11 is glutamine). Percent binding of total counts $^{65}Zn^{2+}$/min added is corrected for the amounts (in nanomoles) of peptides adhering to the membrane. (1d) Scatchard plot. As for (1a), with $Aβ_{1-28}$ peptide substituting for $Aβ_{1-40}$. 157 nM $^{65}Zn$ (138,000 cpm) is used in this experiment to probe immobilized peptide (1.6 nmol). (1e) Graph showing the pH dependence of $^{65}Zn^{2+}$ binding to $Aβ_{1-40}$.

Figure 1B:
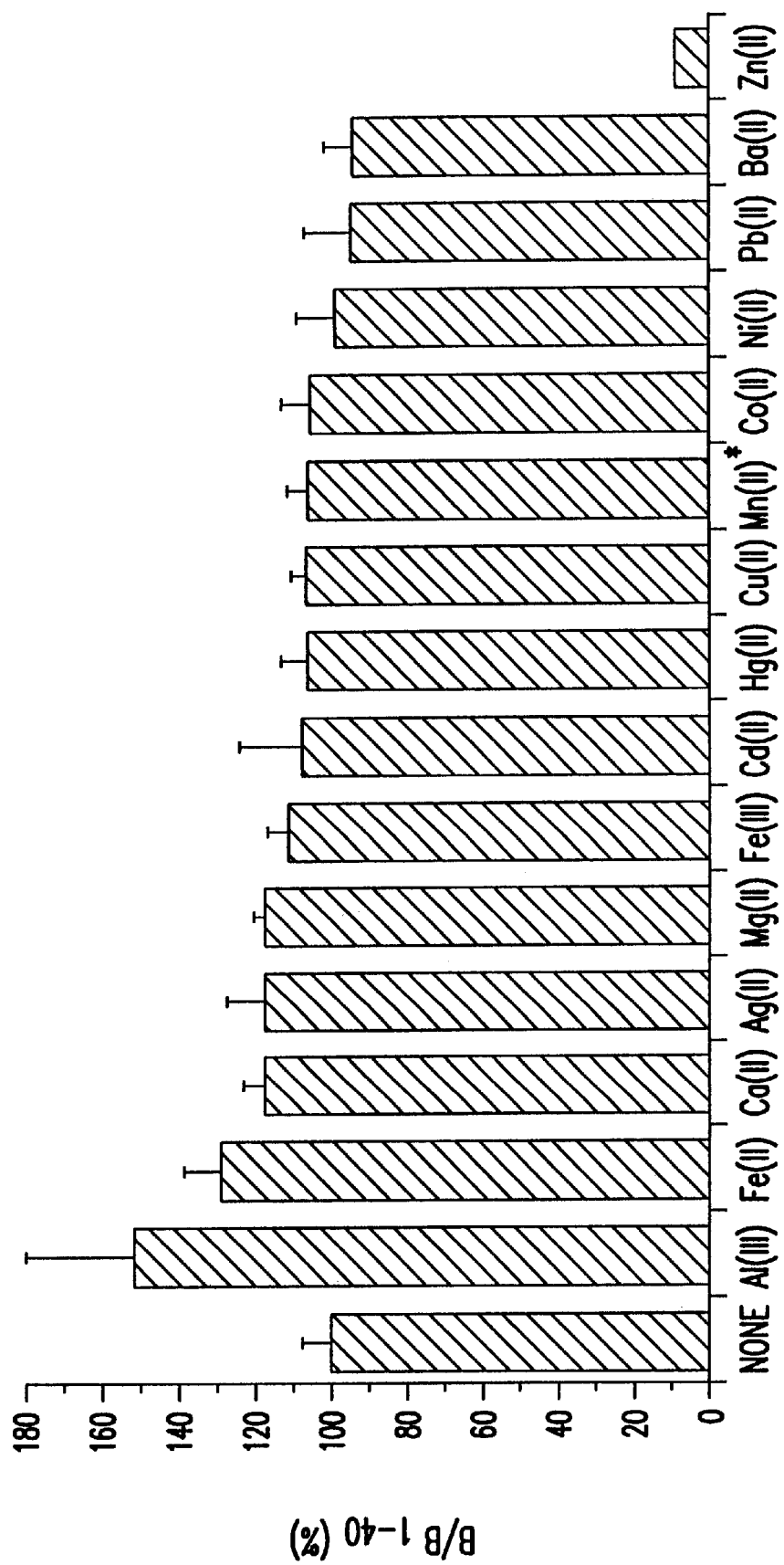

Results shown are indicative of n>3 experiments where 55 μg of Aβ is applied to the column and eluted in 15 ml, monitored by 254 nm absorbance. (2a) A graph showing the chromatogram of Aβ in the presence of EDTA, 50 μM, $Zn^{2+}$, 0.4 μM; $Zn^{2+}$, 25 μM; and $Cu^{2+}$, 25 μM. The elution points of molecular mass standards and relative assignments of Aβ peak elutions are indicated. Mass standards were blue dextran ($2\times10^6$ kDa, $V_0$=void volume), BSA (66 kDa), carbonic anhydrase (29 kDa), cytochrome c (12.4 kDa), and aprotinin (6.5 kDa). The mass of Aβ is 4.3 kDa. (2b) Bar graph showing the relative amounts (estimated from areas under the curve) of soluble Aβ eluted as monomer, dimer, or polymer in the presence of various metal ions (25 μM), varying concentrations of $Zn^{2+}$ or $Cu^{2+}$ (the likelihood of Tris chelation is indicated by upper limit estimates), and EDTA; Data for experiments performed in the presence of copper were taken from 214 nm readings and corrected for comparison. (2c) Bar graph showing the effects of pre-blocking the chromatography column with BSA upon the recovery of Aβ species in the presence of zinc (25 μM), copper (25 μM), or chelator.

Figure 3A:
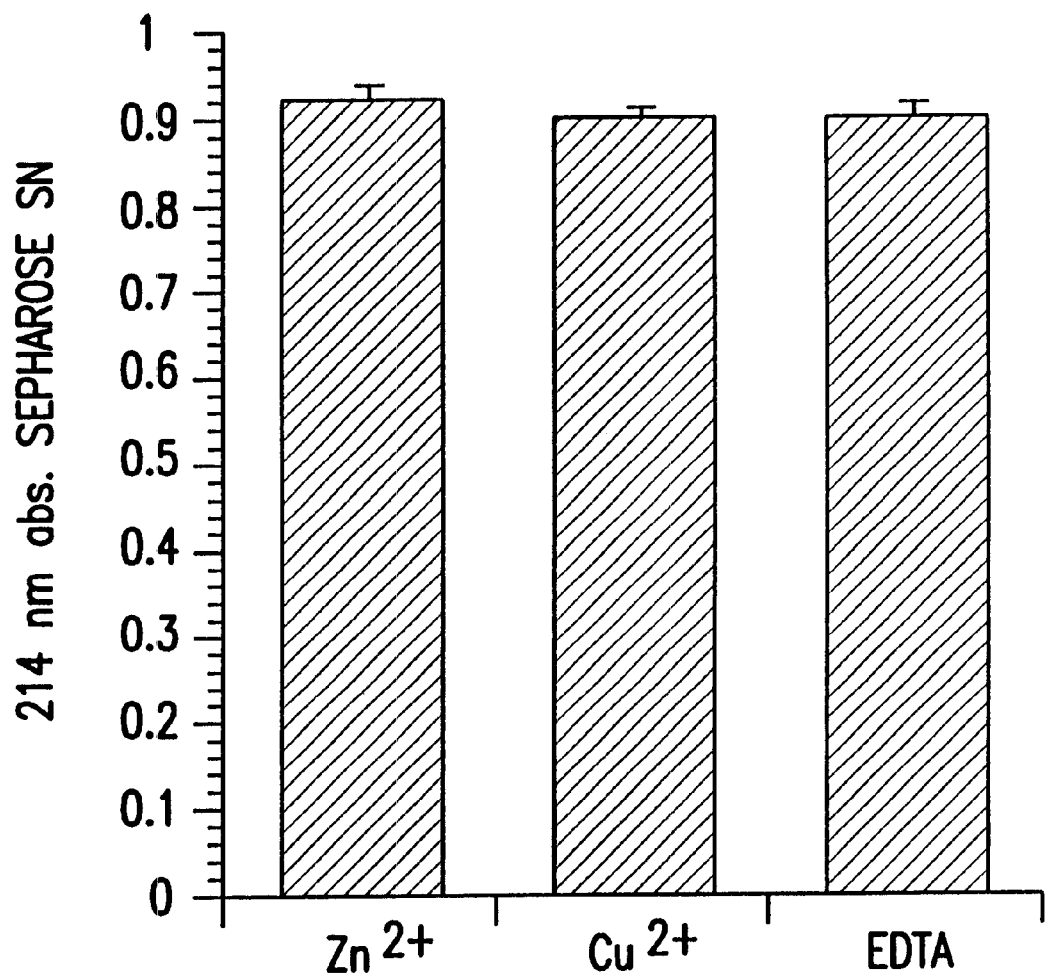
Figure 3B:
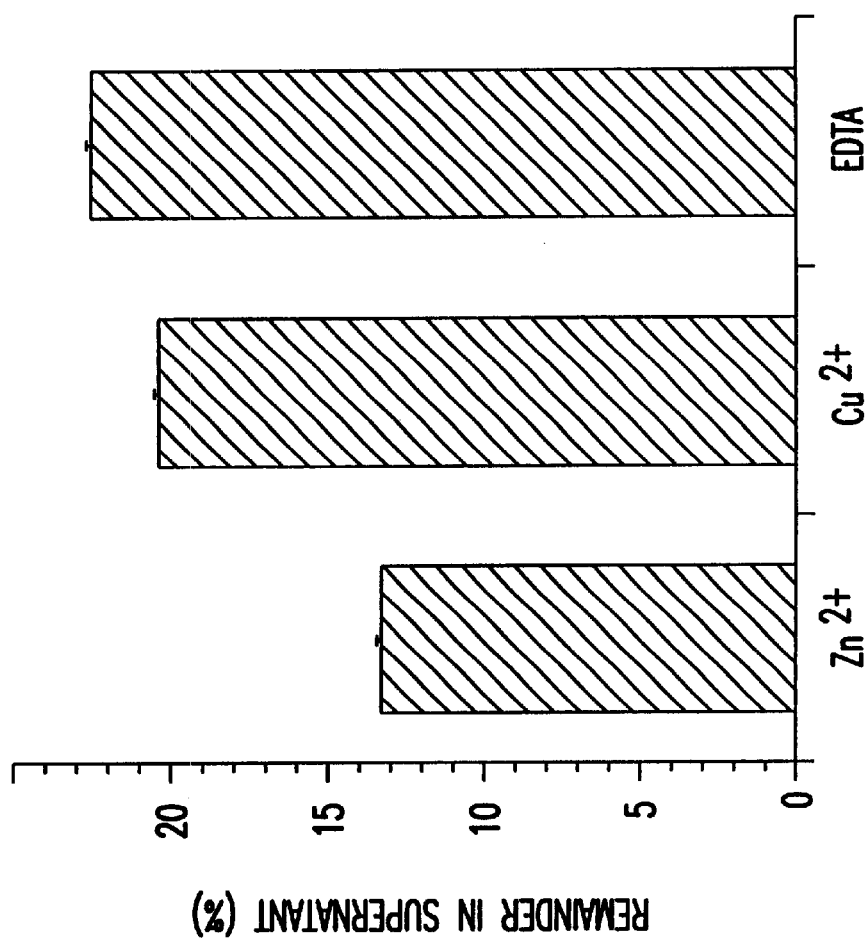

FIGS. 3a and 3b. Aβ binding to kaolin (aluminum silicate): effects of zinc (25 μM), copper (25 μM), and EDTA (50 μM). (3a) Bar graph showing the concentration (by 214 nm absorbance) of Aβ remaining in supernatant after incubation with 10 mg of G50 Sephadex. (3b) Bar graph showing the concentration (by 214 nm absorbance) of Aβ remaining in supernatant after incubation with 10 mg of kaolin, expressed as percent of the starting absorbance.

Figure 4A:
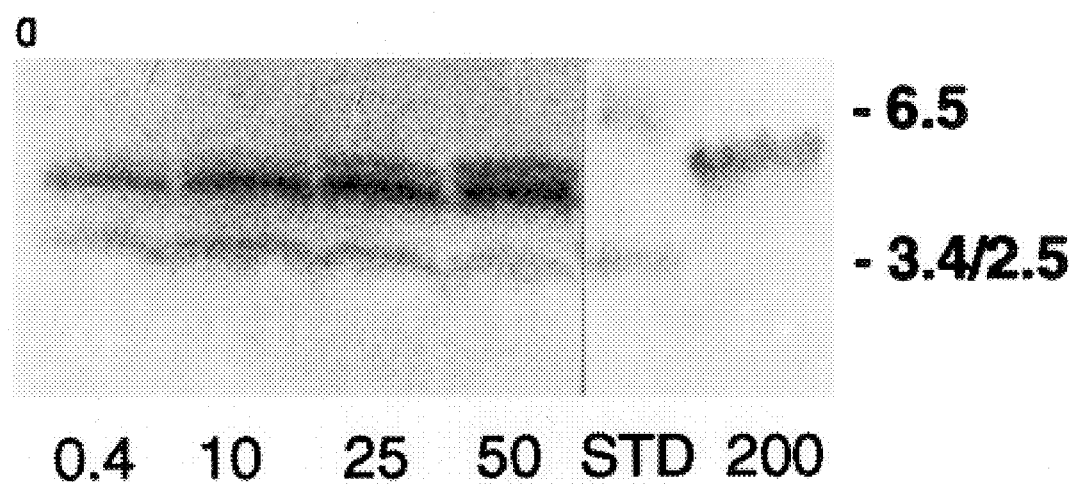
Figure 4B:
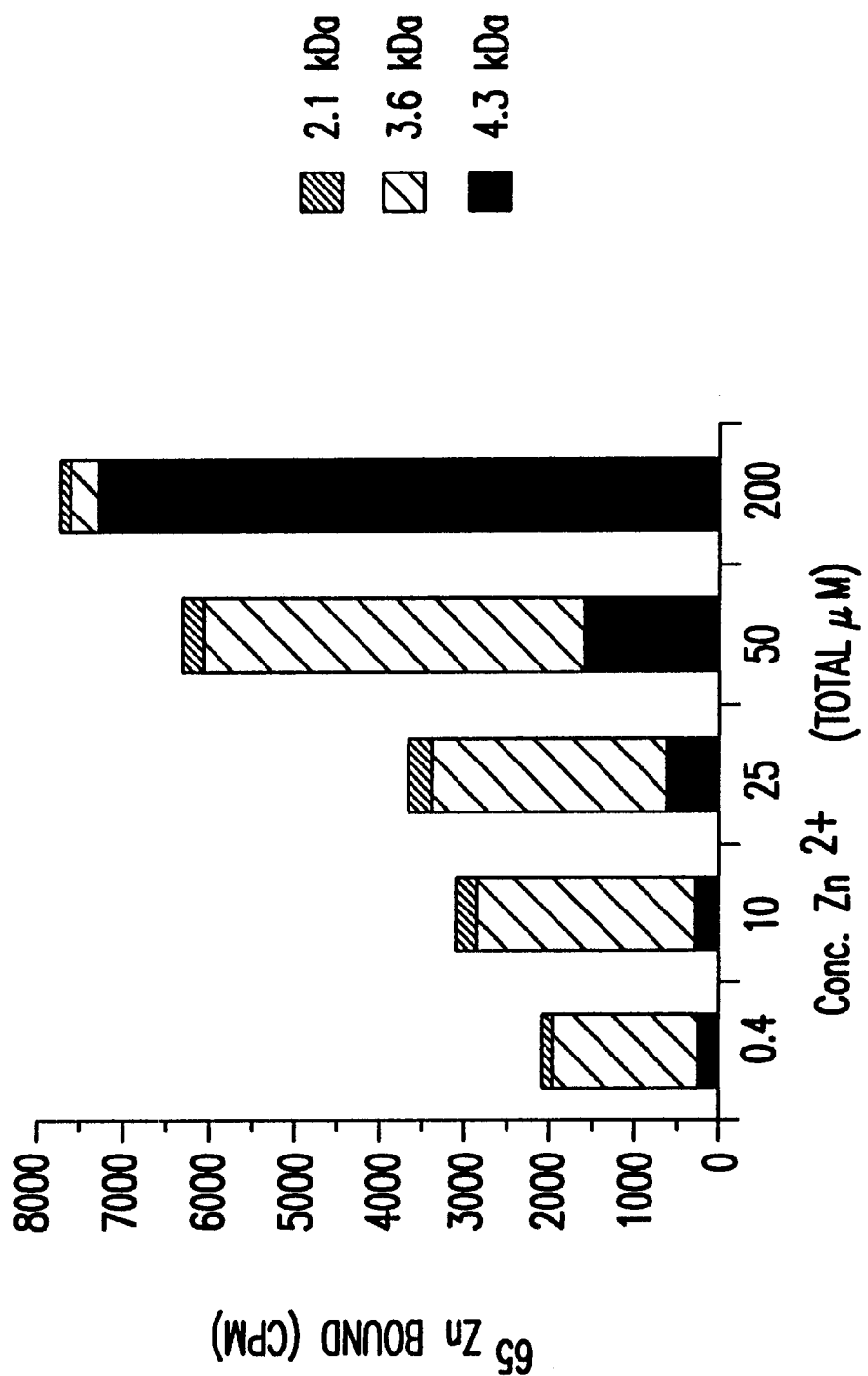

FIGS. 4a and 4b. Effect of $Zn^{2+}$ upon Aβ resistance to tryptic digestion. (4a) A blot of tryptic digests of Aβ (13.9 μg) after incubation with increasing concentrations of zinc (lane labels, in micromolar), stained by Coomassie Blue. Digestion products of 3.6 kDa ($Aβ_{6-40}$), and 2.1 kDa ($Aβ_{17-40}$), as well as undigested $Aβ_{1-40}$ (4.3 kDa), are indicated on the left. The migration of the low molecular size markers (STD) are indicated (in kilodaltons) on the right. (4b) A bar graph showing $^{65}Zn^{2+}$ binding to Aβ tryptic digestion products. The blot in a was incubated with $^{65}Zn^{2+}$, the visible bands excised, and the bound counts for each band determined. These data are typical of n=3 replicated experiments.

Figure 5:
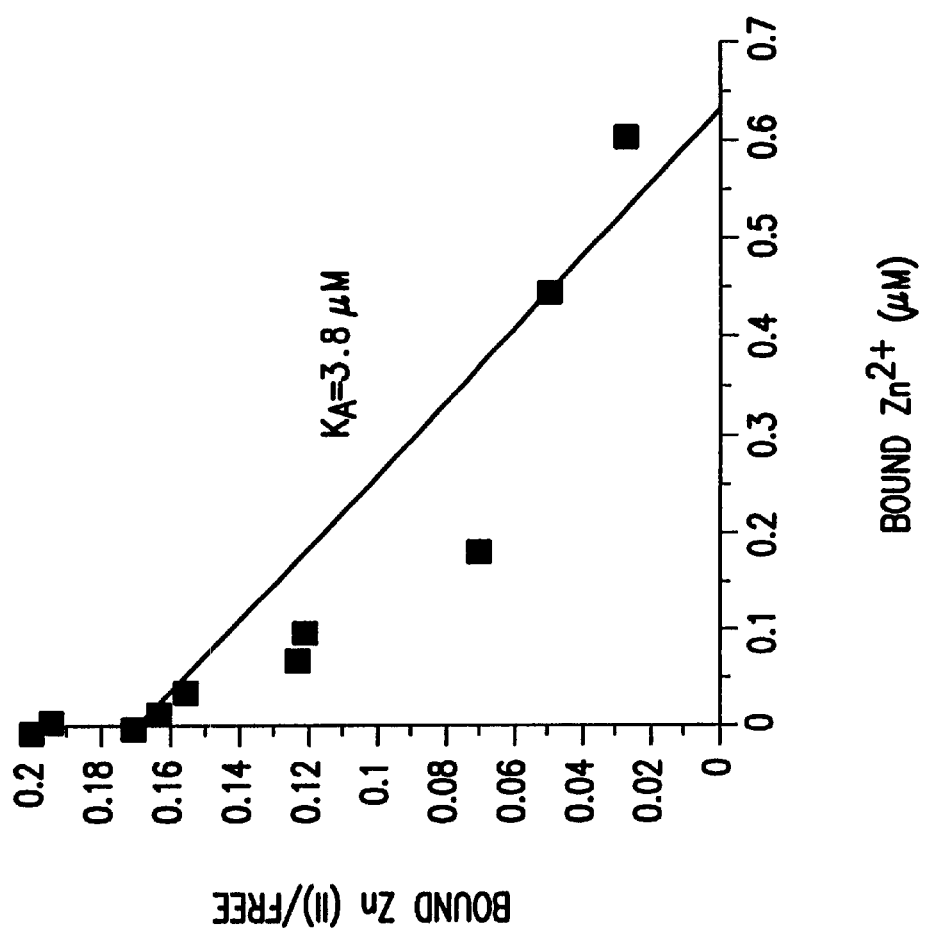

FIG. 5. Scatchard analysis of $^{65}Zn$ binding to rat $Aβ_{1-40}$. Dissolved peptides (1.2 nMol) were dot-blotted onto 0.20μ PVDF membrane (Pierce) and competition analysis performed as described in Example 1 (FIG. 1). Rat $Aβ_{1-40}$ and human $Aβ_{1-40}$ were synthesized by solid-phase Fmoc chemistry. Purification by reverse-phase HPLC and amino acid sequencing confirmed the synthesis. The regression line indicates a $K_A$ of 3.8 μM. Stoichiometry of binding is 1:1. Although the data points for the Scatchard curve are slightly suggestive of a biphasic curve, a biphasic iteration yields association constants of 2 and 9 μM, which does not justify an interpretation of physiologically separate binding sites.

FIGS. 6a, 6b, 6c and 6d. Effect of zinc upon human, $^{125}I$-human and rat $Aβ_{1-40}$ aggregation into >0.2μ particles. Stock human and rat $Aβ_{1-40}$ peptide solutions (16 μM) in water were pre-filtered (Spin-X, Costar, 0.2μ cellulose acetate, 700 g), brought to 100 mM NaCl, 20 mM Tris-HCl, pH 7.4 (buffer 1) ±EDTA (50 μM) or metal chloride salts, incubated (30 minutes, 37° C.) and then filtered again (700 g, 4 minutes). The fraction of the $Aβ_{1-40}$ in the filtrate was calculated by the ratio of the filtrate $OD_{214}$ (the response of the $OD_{214}$, titrated against human and rat $Aβ_{1-40}$ concentrations (up to 20 μM in the buffers used in these experiments), was determined to be linear) relative to the $OD_{214}$ of the unfiltered sample. All data points are in triplicate, unless indicated. (6a) A graph showing the proportions of $Aβ_{1-40}$, incubated ±$Zn^{2+}$ (25 μM) or EDTA (50 μM) and then filtered through 0.2μ, titrated against peptide concentration. (6b) A graph showing the proportion of $Aβ_{1-40}$ (1.6 μM) filtered through 0.2μ, titrated against $Zn^{2+}$ concentration. $^{125}I$-human $Aβ_{1-40}$ ($^{125}I$-human $Aβ_{1-40}$ was prepared according to the method in Mantyh et al., J. Neurochem 61:1171 (1993) (15,000 CPM, the kind gift of Dr. John Maggio, Harvard Medical School) was added to unlabeled $Aβ_{1-40}$ (1.6 μM) as a tracer, incubated and filtered as described above. The CPM in the filtrate and retained on the excised filter were measured by a γ-counter. (6c) A bar graph showing the proportion of $Aβ_{1-40}$ (1.6 μM) filtered through 0.2μ it following incubation with various metal ions (3 μM). The atomic number of the metal species is indicated. (6d) A graph showing the effects of $Zn^{2+}$ (25 μM) or EDTA (50 μM) upon kinetics of human $Aβ_{1-40}$ aggregation measured by 0.2μ filtration. Data points are in duplicate.

FIGS. 7a, 7b, 7c and 7d. Size estimation of zinc-induced Aβ aggregates. (7a and 7b) Bar graphs showing the proportion of $Aβ_{1-40}$ (1.6 μM in 100 mM NaCl, 20 mM Tris-HCl, pH 7.4 (buffer 1), incubated ±$Zn^{2+}$ (25 μM) or EDTA (50 μM) and then filtered through filters of indicated pore sizes (Durapore filters (Ultrafree-MC, Millipore) were used for this study, hence there is a slight discrepancy between the values obtained with the 0.22μ filters in this study compared to values obtained in FIG. 6 using 0.2μ Costar filters). (7c) A bar graph showing $^{65}ZnCl_2$ (130,000 CPM, 74 nM) used as a tracer of the assembly of the zinc-induced aggregates of human $Aβ_{1-40}$ produced in FIGS. 7a and 7b. By determining the amounts of $Aβ_{1-40}$ and $^{65}Zn$ in the filtrate, the quantities retarded by the filters could be determined, and the stoichiometry of the zinc: Aβ assemblies estimated. (7d) Bar graph. Following this procedure, the filters, retaining Zn: Aβ assemblies, were washed with buffer 1 (100 mM NaCl, 20 mM Tris-HCl, pH 7.4)+EDTA (50 μM×300 μl, 700 g, 4 minutes). The amounts of zinc-precipitated $Aβ_{1-40}$ resolubilized in the filtrate fraction were determined by $OD_{214}$, and expressed as a percentage of the amount originally retained by the respective filters. $^{65}Zn$ released into the filtrate was measured by γ-counting.

Figure 8A:
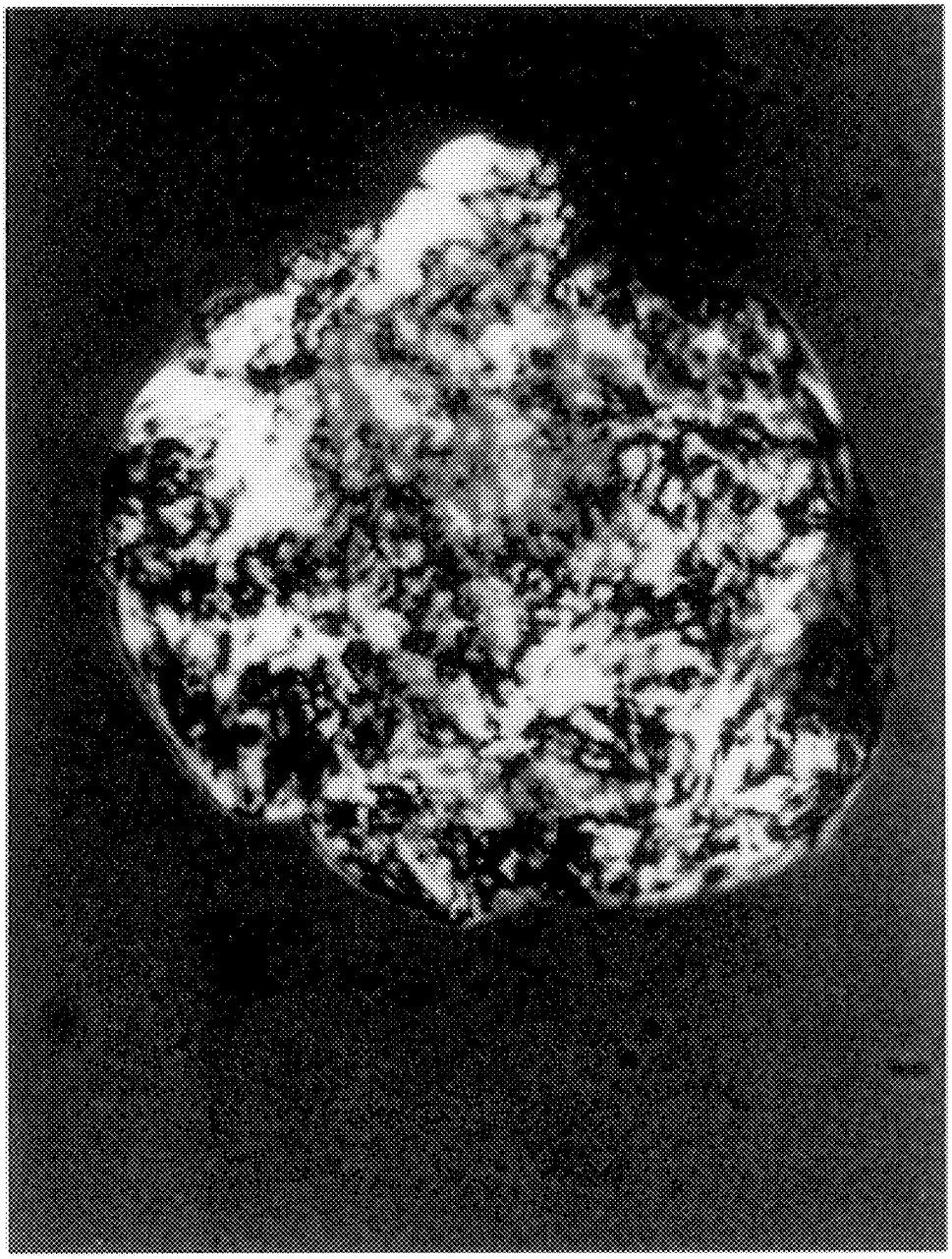
Figure 8B:
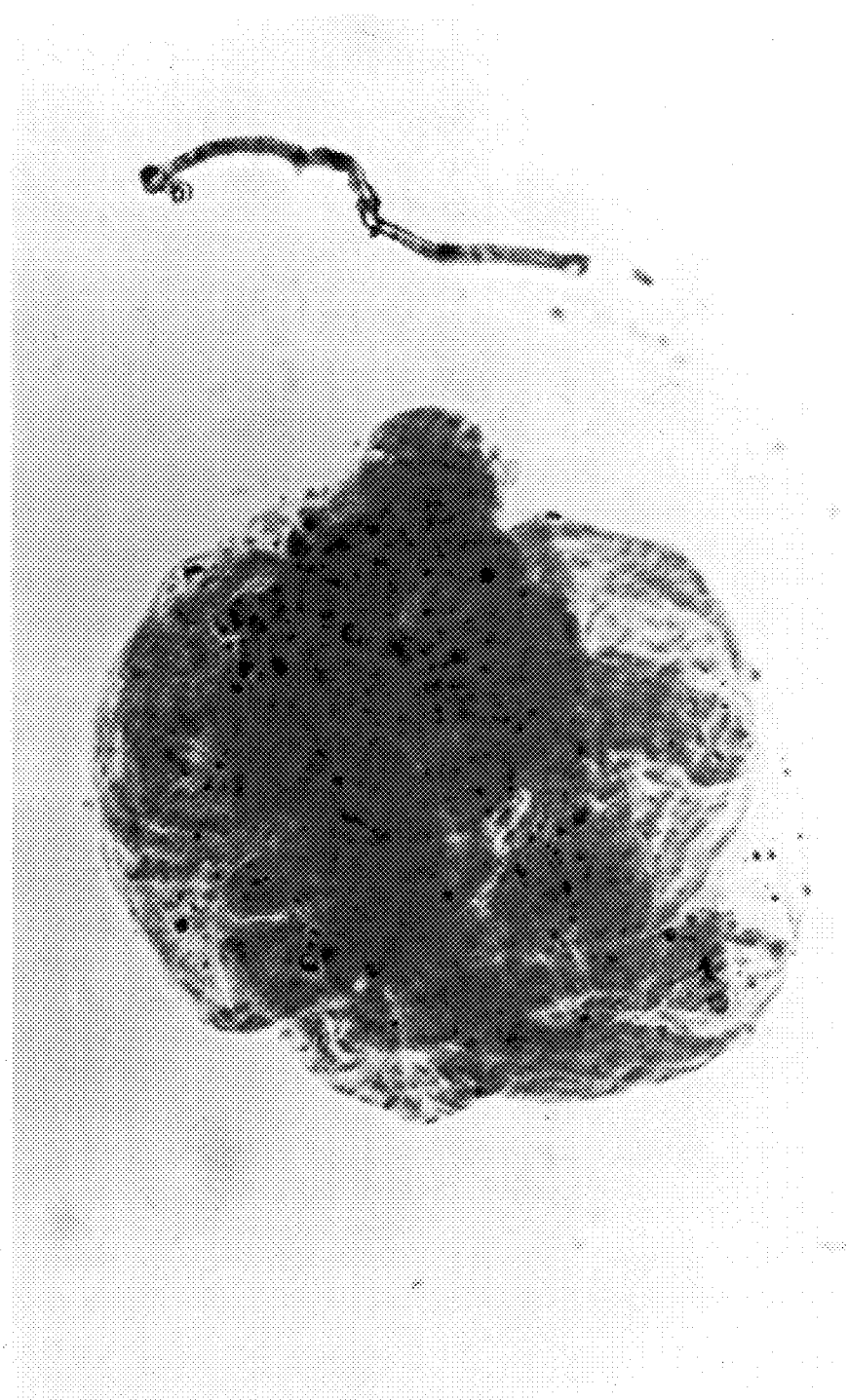

FIGS. 8a and 8b. Zinc-induced tinctorial amyloid formation. (8a) Zinc-induced human $Aβ_{1-40}$ precipitate stained with Congo Red. The particle diameter is 40μ. $Aβ_{1-40}$ (200 μl×25 μM in buffer 1 (100 mM NaCl, 20 mM Tris-HCl, pH 7.4)) was incubated (30 minutes, 37° C.) in the presence of 25 μM $Zn^{2+}$. The mixture was then centrifuged (16,000 g×15 minutes), the pellet washed in buffer 1 (100 mM NaCl, 20 mM Tris-HCl, pH 7.4)+EDTA (50 μM), pelleted again and resuspended in Congo Red (1% in 50% ethanol, 5 minutes). Unbound dye was removed, the pellet washed with buffer 1 (100 mM NaCl, 20 mM Tris-HCl, pH 7.4) and mounted for microscopy. (8b) The same aggregate visualized under polarized light, manifesting green birefringence. The experiment was repeated with EDTA (50 μM) substituted for $Zn^{2+}$ and yielded no visible material.

Figure 9:
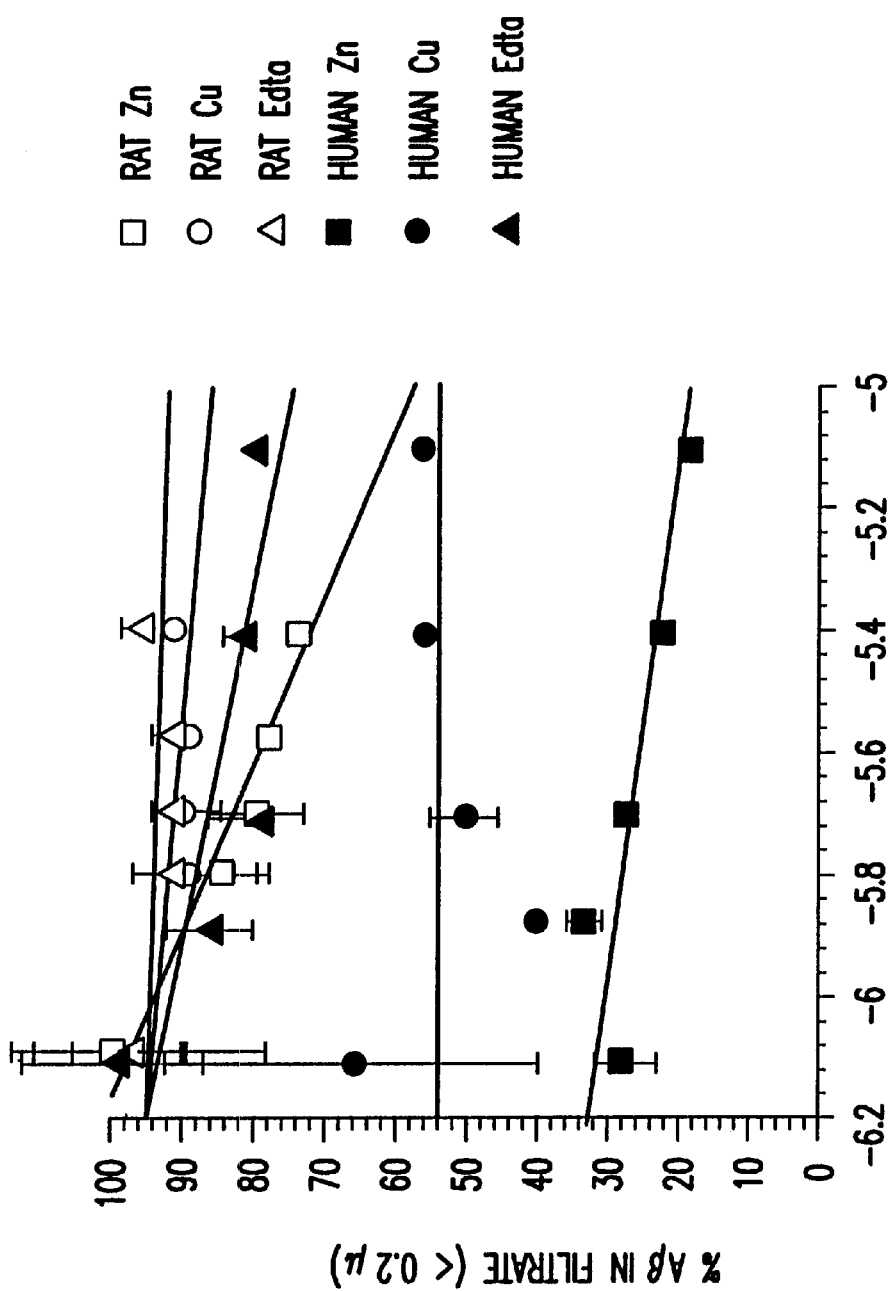

FIG. 9. A graph showing the effect of zinc and copper upon human, $^{125}I$-human and rat $Aβ_{1-40}$ aggregation into >0.2μ it particles. Stock human and rat $Aβ_{1-40}$ peptide solutions (16 μM) in water were pre-filtered (Spin-X, Costar, 0.2μ cellulose acetate, 700 g), brought to 100 mM NaCl, 20 mM Tris-HCl, pH 7.4 (buffer 1)±EDTA (50 μM) or metal chloride salts, incubated (30 minutes, 37° C.) and then filtered again (700 g, 4 minutes). The fraction of the $Aβ_{1-40}$ in the filtrate was calculated by the ratio of the filtrate $OD_{214}$ (the response of the $OD_{214}$, titrated against human and rat $Aβ_{1-40}$ concentrations (up to 20 μM in the buffers used in these experiments), was determined to be linear) relative to the $OD_{214}$ of the unfiltered sample. All data points are in triplicate, unless indicated. (FIG. 9) The graph shows the proportions of $A\beta_{1-40}$ incubated $\pm Zn^{2+}$ (25 µM) or $Cu^{2+}$ or EDTA (50 µM) and then filtered through 0.2µ, titrated against peptide concentration.

Figure 10:
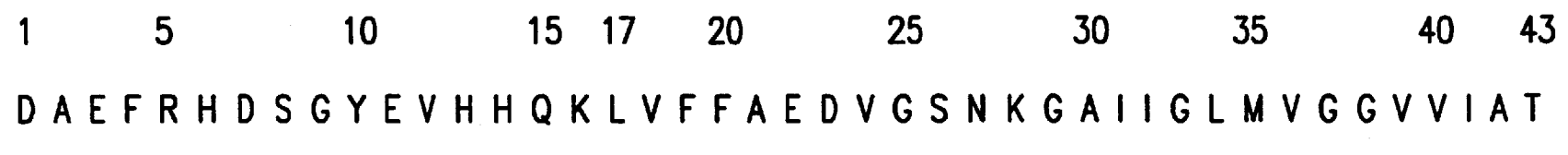

FIG. 10. The amino acid sequence of human Aβ peptide SEQ ID NO:1. The amino acid sequence of human Aβ peptide is depicted and amino acid positions are numbered.

Other features and advantages of the invention will be apparent from the following detailed description, and from the claims.

DETAILED DESCRIPTION OF THE PREFERRED EMBODIMENTS $\beta_{1-40}$ a major component of Alzheimer's disease cerebral amyloid, is present in the CSF and remains relatively soluble at high concentrations ($\leq 3.7$ mM). Thus, physiological factors which induce Aβ amyloid formation provide valuable clues to the pathogenesis of the disease. It has been discovered that human Aβ specifically and saturably binds zinc. Concentrations of zinc above 300 nM rapidly destabilize human $A\beta_{1-40}$ solutions, inducing tinctorial amyloid formation. Meanwhile, rat $A\beta_{1-40}$ binds zinc less avidly and is immune to these effects, perhaps explaining the scarcity with which these animals form cerebral Aβ amyloid. Collectively, these data suggest a potentially critical role for cerebral zinc metabolism in the neuropathogenesis of Alzheimer's disease.

Further, it has been observed that abnormalities of zinc homeostasis occur in AD and DS patients. It has now been shown that Aβ specifically and saturably binds zinc, manifesting high-affinity binding ($K_A$=107 nM) compatible with normal CSF zinc levels, and low-affinity binding ($K_A$=5.2 µM). Cerebral zinc homeostasis, which has been reported to be abnormal in AD (D. Wenstrup, W. D. Ehmann, W. R. Markesbery, *Brain Res.* 533:125 (1990); J. Constantinidis, *Encephale* 16:231 (1990); F. M. Corrigan, G. P. Reynolds, N. I. Ward, *Biometals* 6:149 (1993); C. O. Hershey et al., *Neurology* 33:1350 (1983)) may be important for the metabolic fate of Aβ since increased concentrations of zinc promote the peptide's adhesiveness and resistance to proteolytic digestion. Moreover, oral zinc supplementation has recently been shown to have an acutely adverse effect on cognition in AD subjects, but not age-matched controls indicated that environmental or nutritional zinc exposure may be a contributing factor to AD pathophysiology.

The present findings have indicated that Aβ strongly and specifically binds zinc in a pH dependent manner. In the brain milieu, these metal ions are present in sufficient concentration to exert these effects on binding and solubility. A decrease in Aβ solubility occurs in the presence of concentrations of zinc as low as 0.3 µM. Occupation of the zinc binding site on Aβ increases the resistance of the peptide to tryptic digestion at the α-secretase site. α-Secretase is an, as yet, unidentified protease which has been observed to cleave the precursor molecule of Aβ, the Amyloid Protein Precursor (APP) within the Aβ domain, rendering Aβ incapable of accumulating. Hence, occupation of the zinc binding site on Aβ will increase the biological half-life of the peptide and so increase its availability for deposition.

Hence, pharmacological agents which prevent binding of zinc to its binding sites on Aβ or which prevent amyloid formation after Aβ has contacted excess zinc, i.e. greater than 300 nM, could be useful in the treatment of Alzheimer's disease, Down's syndrome, and GALS/PDC by preventing and/or reversing the Aβ depositions. There currently exists no means for rapidly screening candidate anti-amyloidotic agents with therapeutic potential in these diseases. The present invention provides such means and methods for screening such candidate pharmaceutical agents.

The effects of candidate anti-amyloidotic pharmacological agents upon zinc-induced Aβ amyloid formation may be rapidly screened by the present filtration assay. The zinc-induced $A\beta_{1-40}$ aggregation reaction is performed in the presence of the candidate agent, with and without ($\pm$) $A\beta_{1-40}$ and filtration titrations performed while varying the concentration of the drug, the zinc, and the peptide (whose concentration is brought to physiological levels by the use of $^3$H-Aβ). The assay may also be performed in the presence of human CSF, to bring any anti-amyloidotic effect observed to a closer in vitro approximation of the actual physiological situation.

Stock human and rat $A\beta_{1-40}$ peptide solutions (16 µM) in water were pre-filtered (Spin-X, Costar, 0.2µ cellulose acetate, 700 g), brought to 100 mM NaCl, 20 mM Tris-HCl, pH 7.4+zinc chloride (0.3 to 25 µM, sampling interval between these concentration limits), ±candidate anti-amyloidotic agent, incubated (30 minutes, 37° C.) and then filtered again (700 g, 4 minutes). The fraction of the $A\beta_{1-40}$ in the filtrate was calculated by the ratio of the filtrate $OD_{214}$ relative to the $OD_{214}$ of the unfiltered sample. The response of the $OD_{214}$, titrated against human $A\beta_{1-40}$ concentrations (up to 20 µM in the buffers used in these experiments) has been determined to be linear. The effect of the candidate anti-amyloidotic agent can be compared to the proportion of peptide that is filtered when the incubation is performed in the presence of EDTA (50 µM) instead of zinc.

Candidate anti-amyloidotic agents will be broad-ranging but can be classified as follows:

Agents which modify the availability of zinc for interaction with Aβ: They include chelating agents such as desferrioxamine, but also include amino acids histidine and cysteine which bind free zinc, and are thought to be involved in bringing zinc from the plasma across the blood-brain barrier (BBB). These agents include all classes of specific zinc chelating agents, and combinations of non-specific chelating agents capable of chelating zinc such as EDTA (Edetic acid, N,N'-1,2-Ethane diylbis[N-(carboxymethyl) glycine] or (ethylenedinitrilo)tetraacetic acid, entry 3490 in Merck Index 10th edition) and all salts of EDTA, and/or phytic acid [myo-Inositol hexakis(dihydrogen phosphate), entry 7269 in the Merck Index 10th edition] and phytate salts.

Solvents: dimethyl sulfoxide has been proposed as a treatment for some forms of systemic amyloidosis; ethanol; glycine (an amino acid which has solvent properties).

Copper: In higher concentrations, copper prevents $A\beta_{1-40}$ adhering to glass and stabilizes a soluble Aβ dimer. Its effects on zinc-induced Aβ aggregation may be competitive.

Lithium carbonate: Lithium bromide has been used to maintain Aβ synthetic peptides in solution (Halverson et al., Biochem. 29:2639–2644 1990). This observation invites the speculation that lithium salts, per se, may inhibit Aβ aggregation. Lithium carbonate is a neuroleptic medication used in the treatment of bipolar affective disorder, where its systemic therapeutic levels are kept at 1 mM. If lithium carbonate at 1 mM has an inhibitory effect on Aβ aggregation, it would be a reasonable candidate as a therapeutic agent for AD and related pathological conditions.

Miscellaneous: Because there is no precedent for an effective anti-amyloidotic pharmaceutical, it is reasonable to serendipitously try out compounds which may have access to the brain compartment for their ability to inhibit zinc-induced Aβ aggregation. These compounds include dye compounds, heparin, heparan sulfate, and anti-oxidants, e.g., ascorbate, trolox and tocopherols.

DEFINITIONS

Aβ peptide is also known in the art as Aβ, β protein, β-A4 and A4.

Amyloid as is commonly known in the art, and as is intended in the present specification, is a form of aggregated protein.

Similarly, Aβ Amyloid is an aggregated Aβ peptide. It is found in the brains of patients afflicted with AD and DS and may accumulate following head injuries and in GALS/PDC.

Tinctorial amyloid is referred to amyloid that in addition to being insoluble in aqueous buffer can be stained with Congo Red, and has positive birefringence in polarized light.

Anti-amyloidotic agent refers to a compound that inhibits formation of amyloid.

Zinc-induced Aβ aggregates are, like tinctorial amyloid, insoluble in aqueous buffer and stain with Congo Red. However, unlike tinctorial amyloid, they do not manifest positive birefringence in polarized light.

Aβ amyloidosis, as is commonly known in the art and intended in the present specification, refers to the pathogenic condition in humans and other animals which is characterized by formation of Aβ amyloid in neural tissue such as brain.

Pre-filtering and pre-filtered as used in the present specification means passing a solution, e.g. Aβ peptide in aqueous solution, through a porous membrane by any method, e.g. centrifugation, drip-through by gravitational force, or by application of any form of pressure, such as gaseous pressure.

Physiological solution as used in the present specification means a solution which comprises compounds at physiological pH, about 7.4, which closely represents a bodily or biological fluid, such as CSF, blood, plasma, et cetera.

Heavy metal chealating agent refers to any agent, e.g., compound or molecule, which chelates heavy metals, i.e., renders the heavy metal incapable of reacting and/or binding other agents, e.g., compound or molecule. Examples of such heavy metal chealating agents are EDTA or Desferrioxamine.

In the present invention, the heavy metal salts are of any heavy metal or any transition metal, in any form, soluble or insoluble.

In the present specification, unless otherwise indicated, zinc means salts of zinc, i.e., $Zn^{2+}$ in any form, soluble or insoluble.

Biological fluid means fluid obtained from a person or animal which is produced by said person or animal. Examples of biological fluids include but are not limited to cerebrospinal fluid (CSF), blood, serum, and plasma. In the present invention, biological fluid includes whole or any fraction of such fluids derived by purification by any means, e.g., by ultrafilteration or chromatography.

Neat sample of a biological fluid means that the biological fluid has not been altered, by for example, dilution.

Control human subject refers to a healthy person who is not afflicted with amyloidosis.

In the rapid analytical method for detection of Aβ amyloid, a biological fluid, such as CSF, serum or plasma, of a human patient who is suspected of being afflicted with amyloidosis is titrated in a serial dilution. Similarly, a control sample (biological fluid from a healthy person who is not afflicted with amyloidosis) is titrated by serial dilution. Dilutions may range from a neat (undiluted) sample up to greater than 1:10,000. It is expected that a sample from a person afflicted with amyloidosis would have a lower titre because these patients suffer from a condition which makes them significantly more prone to forming amyloid. Next, an equal amount of Aβ peptide in aqueous buffer or physiological solution is added to each sample. Then, the samples are contacted with large (greater than 300 nM), preferably 25 µM, of a heavy metal cation capable of binding to the peptide comprising at least amino acids 6 to 28 of Aβ peptide. The preferred heavy metal of the present invention is zinc. Hence, the Aβ peptides will form Aβ amyloid in the presence of the heavy metal cations. The Aβ amyloid can then be collected by pelleting them through centrifugation. Finally, the pellets are stained using an Amyloid-staining dye, such as Congo Red, and the pellets are observed under microscope and quantitated (if desired) using a grid. Since, the biological fluid of a patient with amyloidosis (as compared with a healthy person) already has a greater propensity for formation of amyloid, and his/her biological fluid, e.g. CSF, already contains amyloid, therefore, it is expected that the amount of tinctorial Aβ amyloid in the pellets obtained from an afflicted patient be higher than the healthy control samples.

Alternatively, after the samples are titrated in serial dilutions, an equal amount of a titrated Aβ peptide, comprising at least amino acids 6 to 28 of Aβ, is added to each sample. The samples can be as before centrifuged and the counts per minute determined in each pellet. Preferably, however, the samples are filtered and the CPM of the filters are determined by scintillation counter.

In the present methods for determining whether a compound inhibits formation of Aβ amyloid, the amount of soluble or precipitated Aβ peptide remaining in the reaction after exposure to zinc- or heavy metal-induced is measured and compared with the initial amount of the soluble peptide that was added to the reaction mixture, hence, demonstrating that the candidate reagent is able to inhibit formation of amyloid. Conversely, the amount of Aβ amyloid formed in the zinc- or heavy metal-induced reaction is measured and compared with the control reaction mixture containing a chelator of heavy metal cations capable of binding to the peptide comprising at least amino acids 6 to 28 of Aβ, such as EDTA or Desferrioxamine, to determine whether the candidate reagent can inhibit formation of amyloid.

Further, the reaction mixtures can be filtered in order to measure and compare the amounts of the peptide or the amyloid as described above. Conversely, the reaction mixtures can be centrifuged, the pellet stained, with for example Congo Red, and observed under a microscope to detect formation of amyloid. Moreover, the amount of amyloid formed can be quantified by using a grid.

In the present invention, the Aβ peptide may be comprised of any sequence of the Aβ peptide as long as it contains at least the amino acids corresponding to positions 6 through 28 of Aβ peptide which comprise the binding site for zinc, the most preferred heavy metal cation capable of binding to a polypeptide comprising at least amino acids 6 to 28 of Aβ. The preferred embodiments of the invention make use of peptides $A\beta_{1-39}$, $A\beta_{1-40}$, $A\beta_{1-41}$, $A\beta_{1-42}$, and $A\beta_{1-43}$. The most preferred embodiment of the invention makes use of $A\beta_{1-40}$. However, any of the Aβ peptides which comprises at least amino acids 6 to 28 of Aβ may be employed according to the present invention. The sequence of Aβ peptide, including amino acids 6 to 28, is found in C. Hilbich et al., *J. Mol. Biol.* 228:460–473 (1992).

In the present method, the Aβ peptide is detected by using optical spectrophotometry. This is possible because a direct correlation exists between concentration of the peptide and $OD_{214}$ measurements. Although the preferred wave length for the OD measurements is about 214, the measurements may be carried out for the purpose of the present invention at wave lengths from about 190 to about 440. Preferred wave lengths are, however, from about 208 to about 280.

Further, the Aβ peptide may be detected by radiolabelling the peptide and measuring the counts per minute (CPM) of the filtrates and/or the pellets. A preferred radiolabelled Aβ peptide in the present invention is $^3$H-Aβ. Other radiolabels which can be used in the present invention are $^{14}$C and $^{35}$S.

Conversely, one can detect the formation of Aβ amyloid formed in the reaction, using non-specific protein stains, e.g., Coomassie Blue (Bush et al., *J. Biol. Chem.* 269(16):12152–12158 (1994), or antibodies specific for Aβ amyloid (see, e.g. U.S. Pat. No. 5,231,000, issued Jul. 27, 1993). Hence, by measuring the level of Aβ amyloid formation in the reaction according to the present methods, it can be determined whether the candidate agent is effective for inhibiting formation of Aβ amyloid. The level of Aβ amyloid may be quantitated by measuring the amount of Aβ in the soluble or precipitated fraction following centrifugation, or in the filtrate following filtration by ELISA (Suzuki ref.) or by Western Blot.

Other heavy metal cations capable of binding to a polypeptide comprising at least amino acids 6 to 28 of Aβ which may be used in the practice of the invention include metallochloride salts, preferably of zinc, copper, or mercury. The most preferred embodiment of the invention, however, makes use of zinc chloride.

The pH of the various reaction mixtures are preferably close to neutral (about 7.4). The pH, therefore, may range from about 6.8 to about 8, preferably from about 7 to about 7.8, and most preferably about 7.4.

Buffers which can be used in the methods of the present invention include, but are not limited to, Tris-chloride and Tris-base, MOPS, HEPES, bicarbonate, Krebs, and Tyrode's. The concentration of the buffers may be between about 10 mM and about 500 mM. However, considering that these buffers chelate zinc, the concentration of the buffers should be kept as low as possible without compromising the results.

The filters used in the present invention have a pore size which allows passage of Aβ peptides, e.g. from about 0.2 to about 60 microns; preferably from about 0.2 to about 8 microns; and most preferably from about 0.2 to about 0.65 microns. In a preferred embodiment of the invention, a 0.2 micron filter is used. Aβ peptide monomer has a molecular mass of 4.3 kDa. Hence, filters which can retain particles greater than 4.3 kDa, e.g. 4.4 kDa, may be used to practice the present invention. Aβ peptide and fragments can form dimers and polymers. Based on the size of the Aβ peptide used in the present invention, persons of ordinary skill in the art will be able to choose a filter with appropriate pore size so that it allows passage of Aβ peptides and prevents passage of most or all of the amyloid and Aβ aggregates induced by heavy metal cations, such as zinc-induced Aβ aggregate.

Further, any amyloid-staining dye may be used in the methods of the present invention to facilitate the determination of the deposit of amyloid and Aβ aggregates induced by heavy metal cations, such as zinc-induced Aβ aggregate, in solution. Such dyes include but are not limited to congo red, biflavin S and biflavin T. The concentration of such dyes may range from about 0.1% (weight/volume) to about 50% (weight/volume). In fact the upper limit of the dye concentration is limited to solubility limit of the dye in solution.

The present invention permits use of very low concentrations of Aβ peptide, e.g. from about 0.1 nM to 3.7 mM, i.e. the limit of solubility. A preferred embodiment of the invention employs about 0.8 µM concentration of Aβ peptide, a concentration of the peptide which is the lowest detected by optical density. The lowest concentrations reported previously (J. T. Jarrett et al., *Biochem.* 32:4693–4697 (1993)) were 20 micromolar for $Aβ_{1-40}$ and 2 micromolar for $Aβ_{1-42}$. Therefore, an advantage of the present invention is that very low concentrations of the peptide may be used due to the high sensitivity of the assay of the present invention.

Similarly, very low concentrations of the heavy metal cation capable of binding to a polypeptide comprising at least amino acids 6 to 28 of Aβ may be employed, e.g. from about 200 nM and up to the limit of solubility of the heavy metal cation. The most preferred heavy metal cation, zinc, may be used in the present invention at a concentration as low as about 300 nM. The lowest reported concentrations used (P. W. Mantyh et al., *J. Neurochem.* 61:1171 (1993)) was 1 mM, i.e., three orders of magnitude higher than the concentration which may be used in the present invention. One of ordinary skill in the art can easily optimize the concentration of the heavy metal cation with no more than routine experimentation.

The present invention may be practiced at temperatures ranging from about 1 degree centigrade to about 99 degrees centigrade. The preferred temperature range is from about 4 degrees centigrade to about 40 degrees centigrade. The most preferred temperature for the practice of the present invention is about 37 degrees centigrade, i.e. human body temperature.

The aggregation of Aβ peptide occurs at near-instantaneous rate. Hence, results may be obtained by the present methods substantially immediately upon contacting the heavy metal and Aβ peptide. However, if desired, the reaction may be allowed to proceed longer. In a preferred embodiment of the invention, the reaction is carried out for about 30 minutes.

The invention may also be carried out in the presence of biological fluids, such as CSF, to closely simulate actual physiological conditions. The biological fluid may be added directly into the reaction mixtures or may be diluted several fold. Dilutions may range from about 1:10,000 to about 1:1 fold. The preferred biological fluid in the present invention, i.e. CSF, may be used directly or diluted from about 1:1,000 to about 1:5 fold.

The assay of the present invention is ideally suited for the preparation of a kit. Such a kit may comprise a carrier means being compartmentalized to receive in close confinement therein one or more container means, such as vials, tubes, and the like, each of said container means comprising one of the separate elements of the assay to be used in the method. For example, there may be provided a container means containing standard solutions of the Aβ peptide or lyophilized Aβ peptide and a container means containing a standard solution or varying amounts of a heavy metal cation capable of binding to the peptide comprising at least amino acids 6 to 28 of Aβ peptide, in any form, i.e., in solution or dried, soluble or insoluble, in addition to further carrier means containing varying amounts and/or concentrations of reagents used in the present methods, e.g., standard solutions or varying amounts of chealators of heavy metal cations in any form, insolution or dried. Standard solutions of Aβ peptide preferably have concentrations above about 10 μM, more preferably from about 10 to about 25 μM or if the peptide is provided in its lyophilized form, it is provided in an amount which can be solubilized to said concentrations by adding an aqueous buffer or physiological solution. Standard solutions of heavy metal cations preferably have concentrations above 300 nM, more preferably about 25 μM. The standard solutions of analytes may be used to prepare control and test reaction mixtures for comparison, according to the methods of the present invention for determining whether a compound inhibits formation of Aβ amyloid.

One $Zn^{2+}$ binding site in the APP ectodomain has already been described (Bush et al., *J. Biol. Chem.* 268:16109–16112 (1993)). The possibility of additional zinc binding sites on APP was investigated. The $A\beta_{1-40}$ structure possesses 3 histidines and several negatively charged residues, structural features that support $Zn^{2+}$ binding. These studies show that Aβ binds zinc in a saturable and specific manner. Moreover, it is demonstrated that physiological concentrations of $Zn^{2+}$ increase the resistance of the peptide to proteolytic catabolism and promote Aβ precipitation by aluminosilicate. Based on these findings, it has been discovered that excessive zinc concentrations accelerate Aβ deposition in AD and related pathological conditions.

Further, the effects of physiological concentrations of zinc upon the stability of synthetic human $A\beta_{1-40}$ in solution were studied, using the rat/mouse species of the peptide ("rat Aβ") for comparison. Soluble $A\beta_{1-40}$ is produced by rat neuronal tissue (C. Haass and D. J. Selkoe, personal communication), however, Aβ amyloid deposition is not a feature of aged rat brains (D. W. Vaughan and A. Peters, *J. Neuropathol. Exp. Neurol.* 40:472 (1981)). β-amyloidogenesis occurs in other aged mammals possessing the human Aβ sequence, which is strongly conserved in all reported animal species, except rat and mouse (E. M. Johnstone, M. O. Chaney, F. H. Norris, R. Pascual, S. P. Little, *Mol. Brain Res.* 10:299 (1991)). The rat/mouse Aβ substitutions (Arg→Gly, Tyr→Phe and His→Arg at positions 5, 10 and 13, respectively [B. D. Shivers et al., *EMBO J.* 7:1365 (1988)]) appear to cause a specific change in the peptide's physicochemical properties sufficient to confer upon the peptide its relative immunity to amyloid formation. Since zinc binding to human $A\beta_{1-40}$ is histidine-mediated; rat Aβ therefore may be expected to manifest altered zinc binding properties.

The binding affinity of zinc to rat $A\beta_{1-40}$ was studied in a $^{65}Zn$ competitive assay system as described in Example 1 (FIG. 1), to measure the $K_A$ of zinc binding to human $A\beta_{1-40}$. In contrast to human $A\beta_{1-40}$, the Scatchard analysis of zinc binding to rat $A\beta_{1-40}$ reveals only one binding association ($K_A$=3.8 μM), with 1:1 stoichiometry (FIG. 5).

Figure 6A:
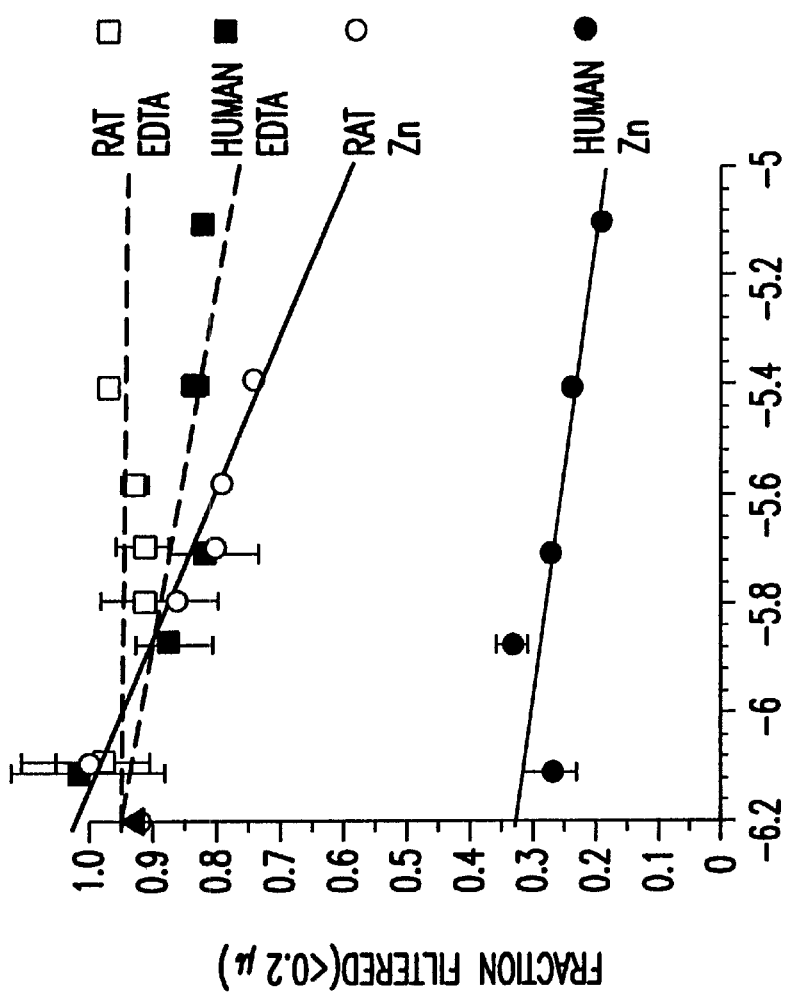

It was observed that the recovery of human $A\beta_{1-40}$ in filtration chromatography is dramatically reduced in the presence of zinc, due, in part, to increased adhesiveness of Aβ. To determine whether the aggregation of human $A\beta_{1-40}$ is also enhanced in the presence of zinc, the peptide was incubated with various concentrations for 30 minutes with $Zn^{2+}$ (25 μM) or EDTA and then filtered the solutions through 0.2μ filters. Zinc caused up to 80% of the available peptide to aggregate into >0.2μ particles (FIG. 6A). (Incubation of $A\beta_{1-40}$ solutions in the filter devices, without actual filtration, indicated that there was no non-specific loss of peptide to the plastic or membrane surfaces.) There appears to be a shallow negative log-linear relationship between human Aβ peptide concentration and the proportion of filterable peptide in 25 μM $Zn^{2+}$, but even at the lowest concentration tested (0.8 μM), >70% of the human $A\beta_{1-40}$ solution aggregated. In contrast, the effect of $Zn^{2+}$ on rat $A\beta_{1-40}$ was unremarkable, with no aggregation of a 0.8 μM peptide solution detected under the same conditions, and only 25% aggregation of a 4 μM solution. Meanwhile, in the presence of EDTA, human and rat $A\beta_{1-40}$ solutions behaved indistinguishably, with no detectable aggregation observed at 0.8 μM, and ≈15% aggregation at higher peptide concentrations.

Next, the formation of >0.2μ Aβ particles was titrated against increasing zinc concentrations (FIG. 6B), and a shallow response curve for human $A\beta_{1-40}$ (1.6 μM) was observed until the zinc concentration reached 300 nM, corresponding to the saturation of high-affinity binding. At zinc concentrations above 300 μM, corresponding to low-affinity binding, human $A\beta_{1-40}$ dramatically aggregates. In contrast, rat $A\beta_{1-40}$ remains stable in the presence of up to 10 μM zinc, and only at 25 μM zinc was aggregation observed.

Figure 6B:
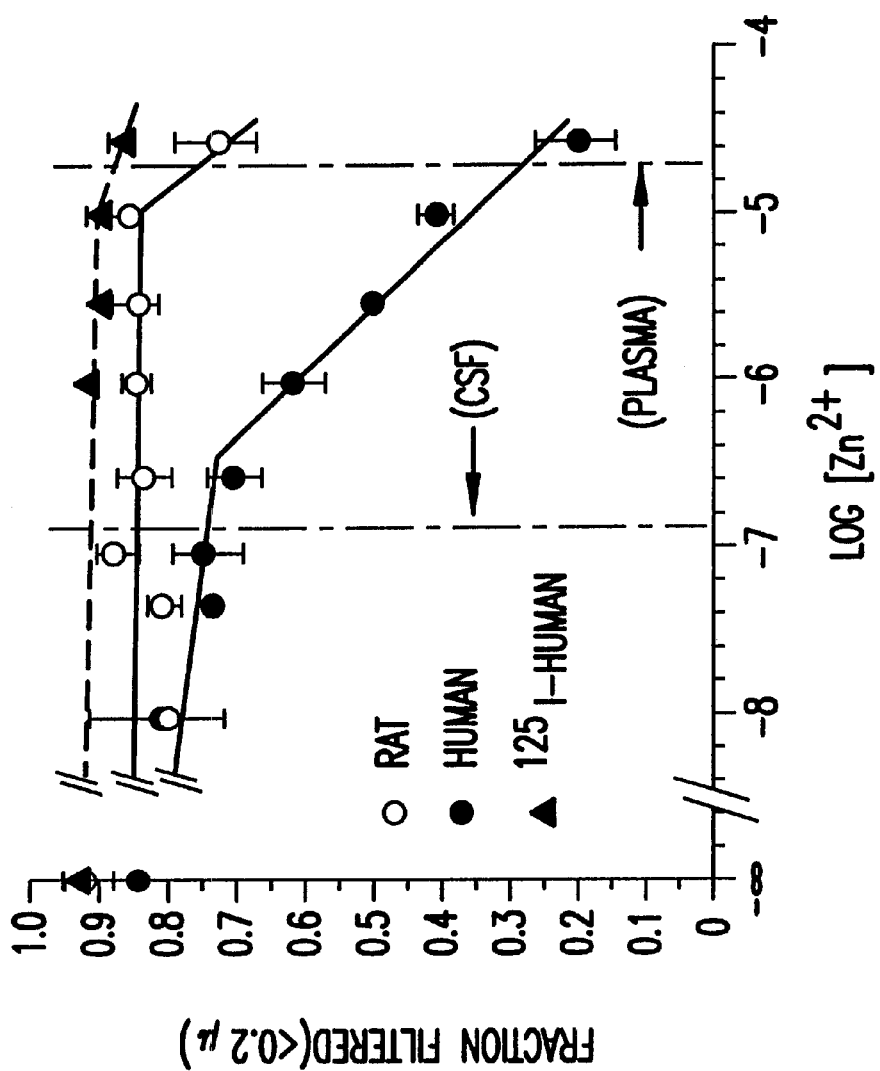
Figure 6C:
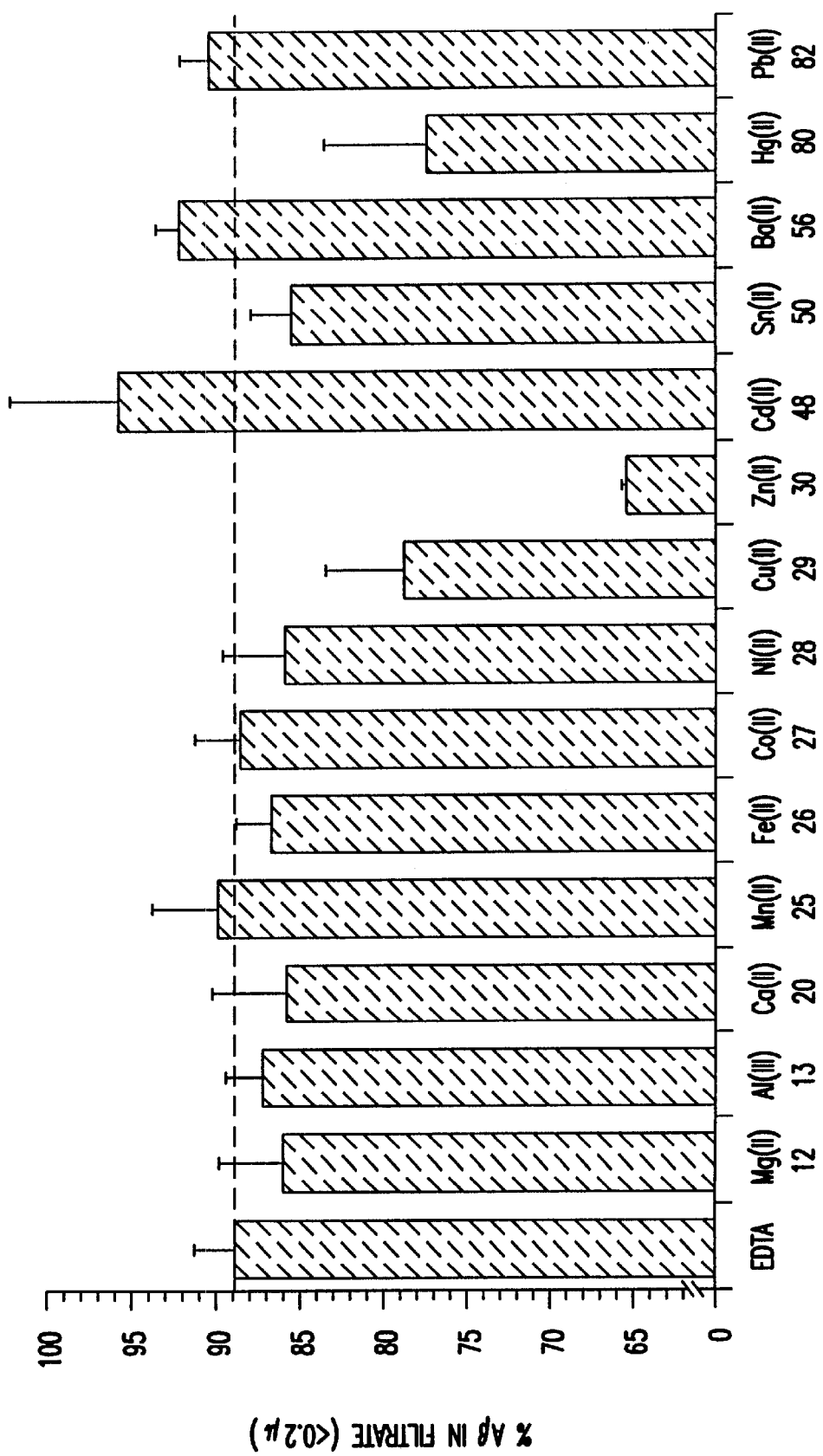
Figure 6D:
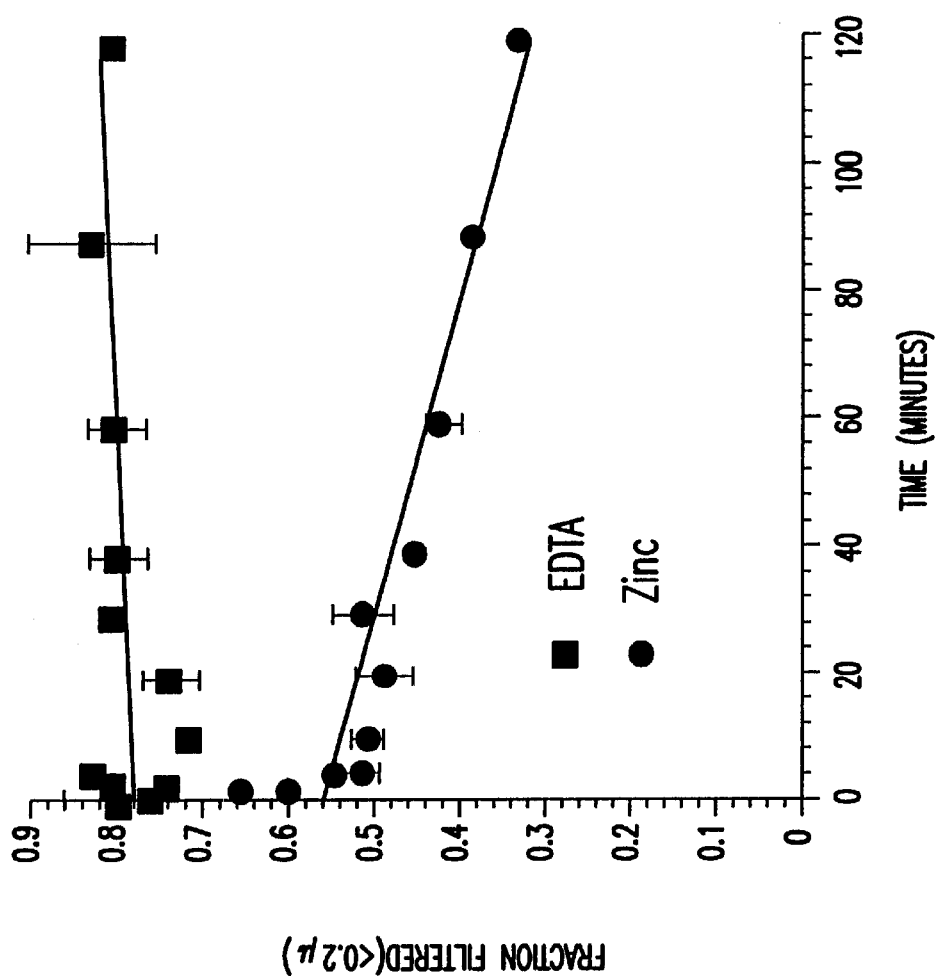

To determine the effects of zinc on $A\beta_{1-40}$ at physiological peptide concentrations requires an assay more sensitive than spectroscopy. (Human $A\beta_{1-40}$ at 0.8 μM in buffer 1 corresponds to 0.090 absorbance units at 214 nm. Aggregation studies of peptides at lower starting concentrations would involve readings at the limits of sensitivity). Thus, the effects of zinc on $^{125}I$-human $A\beta_{1-40}$ used as a tracer in the presence of unlabeled peptide was characterized. Unlike its unlabeled precursor, $^{125}I$-$A\beta_{1-40}$ (at 1.6 μM total peptide) remained stable in the presence of increasing zinc concentrations, indicating that $^{125}I$-$A\beta_{1-40}$ is not a suitable tracer (FIG. 6B). The tracer is iodinated on the tyrosine residue at position 10, which is a phenylalanine in the rat peptide. Thus, the tyrosine residue may be critical to the stability of the human peptide. These data may also explain why a recent report required relatively high concentrations of $Zn^{2+}$ (1 mM) to precipitate $^{125}I$-human $A\beta_{1-40}$ in centrifugation studies (P. W. Mantyh et al., *J. Neurochem.* 61:1171 (1993)). Extrapolating the curve in FIG. 6A to 0.6 nM currently provides the best estimate of the effect of zinc upon physiological Aβ concentrations (M. Shoji et al., *Science* 258:126 (1992); P. Seubert et al., *Nature* 359:325 (1992))., and indicates that 25% of the peptide would aggregate into >0.2μ particles under these conditions. The specific vulnerability of human $A\beta_{1-40}$ for $Zn^{2+}$ is indicated by the observation that $Zn^{2+}$ is the only one of several metal ions tested on an equimolar basis, including $Al^{3+}$, to induce significant aggregation of human $A\beta_{1-40}$ in this system (FIG. 6C).

Next, the kinetics of the assembly of zinc-induced human $A\beta_{1-40}$ aggregates (FIG. 6D) was investigated. (In order to achieve time point measurements of less than 1 minute, the procedure was modified so that samples were centrifuged at 2500 g, allowing the sample volume to be completely filtered in 40 seconds.) The data obtained indicate that following the addition of stock $A\beta_{1-40}$ in water (15.9 μM, pH 5.6) to $Zn^{2+}$ (25 μM) in saline buffer (pH 7.4) there is a near-instantaneous aggregation of the peptide (1.6 μM final concentration) into filterable particles with two phases observed over two hours. The initial phase is rapid, with a half-maximal assembly rate of ≈0.4 μM/min. The steady state of the second phase is achieved within about 2 minutes, whereupon particle assembly proceeds at a rate of 3.2 nM/min with no evidence of saturation within 2 hours. At this rate, the available peptide is exhausted within five hours of initiation. Although the addition of EDTA buffer caused the near-instantaneous aggregation of 20% of the 1.6 μM Aβ$_{1-40}$ solution into >0.2μ particles, no further particle assembly was observed over the time course of the experiment. In comparison, human Aβ$_{1-40}$ (20 μM in PBS, pH 7.4) has been reported to be stable for 10 days (J. T. Jarrett, E. P. Berger, P. T. Lansbury, *Biochemistry* 32:4693 (1993)), and seeding the solution with Aβ$_{1-42}$ (2 μM), the more amyloidogenic Aβ species, induced aggregation of this solution which was half-maximal only after 4–5 days. Thus, the results presented here represent a major advance among attempts to induce amyloid formation in vitro using the wild-type form of the main species of secreted Aβ (Aβ$_{1-40}$).

Figure 7A:
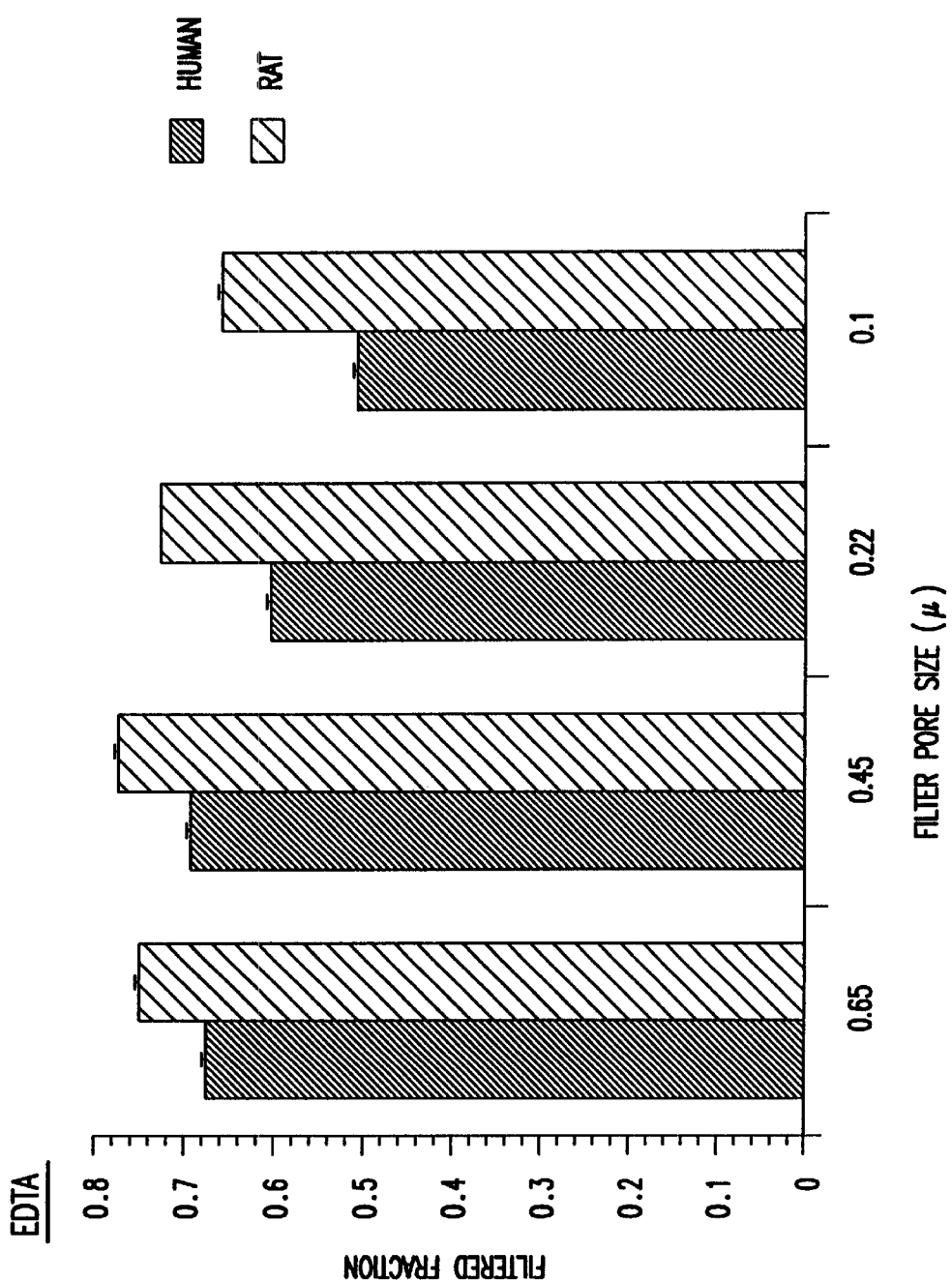
Figure 7B:
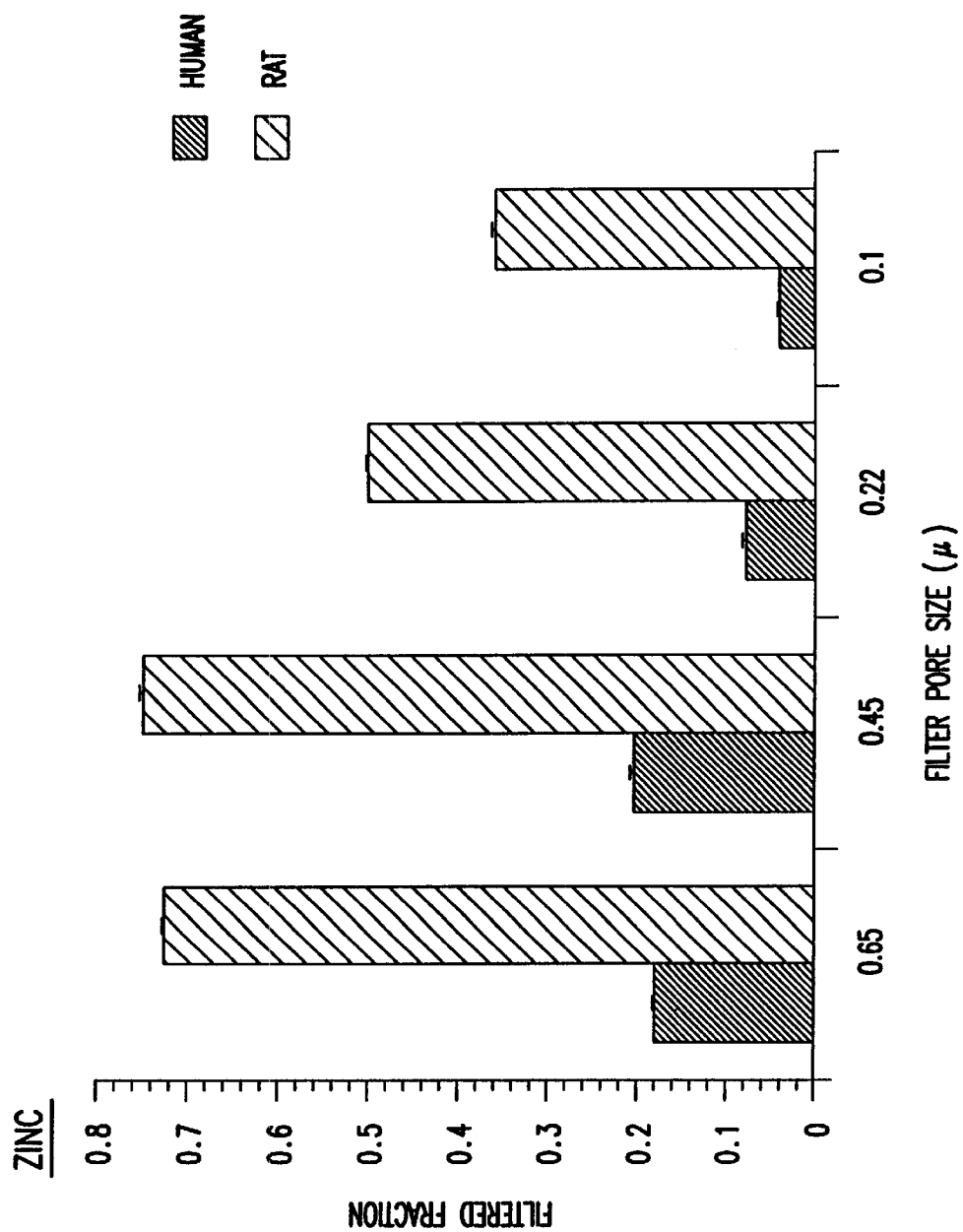
Figure 7C:
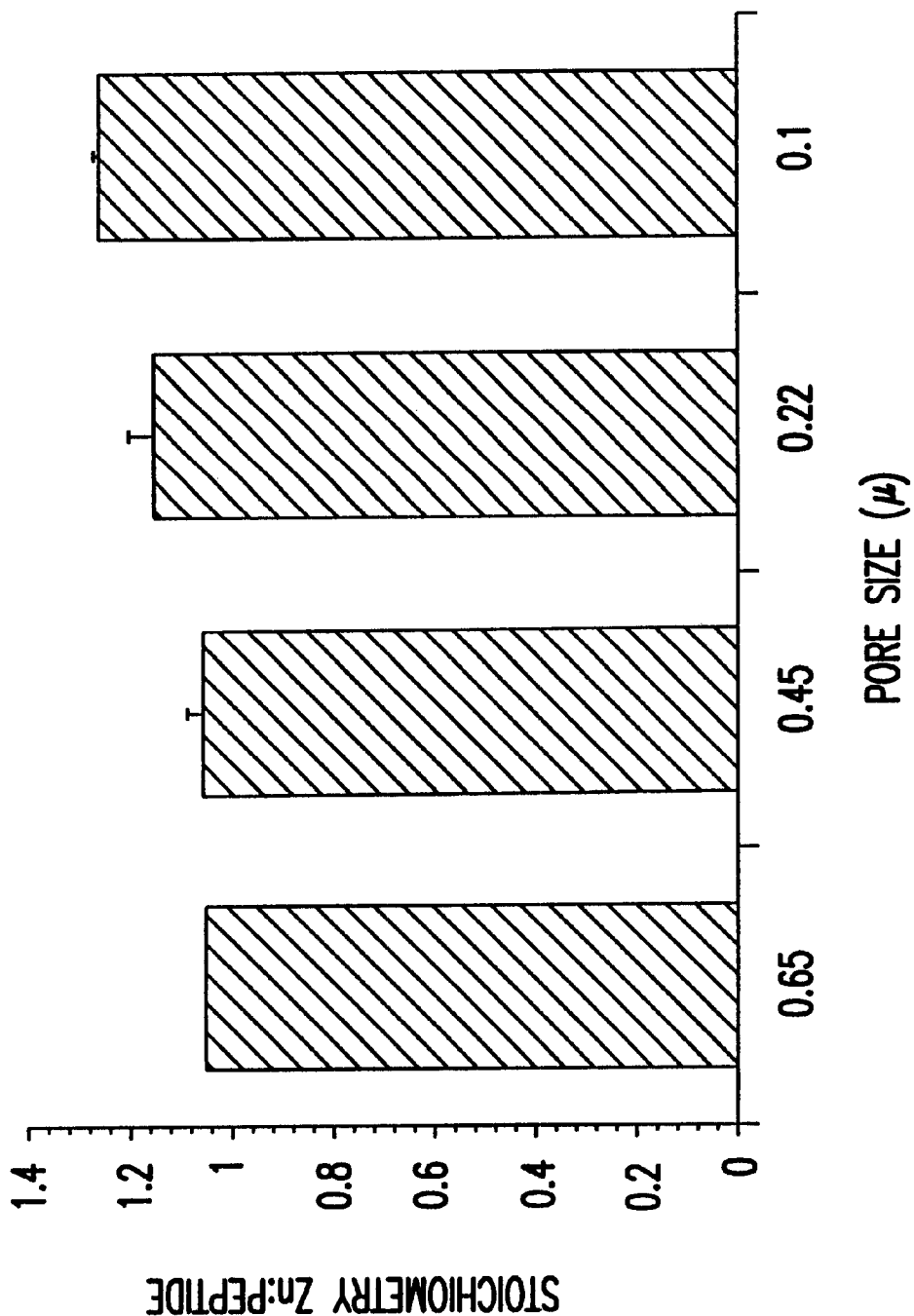

To estimate the size of the Aβ aggregates formed in the presence of zinc, Aβ$_{1-40}$ (1.6 μM) was incubated with Zn$^{2+}$ (25 μM) or EDTA and then passed through filters with various pore sizes (FIGS. 7a and 7b). Following incubation in EDTA, human Aβ$_{1-40}$ assembled into populations of heterogeneous particle sizes, >0.1/μ: 47%, >0.22μ: 40%, >0.65μ: 32%. The comparable proportions of filtered rat Aβ$_{1-40}$ particles were, >0.1μ: 36%, >0.22μ: 27%, >0.65μ: 25%. Upon incubation with Zn$^{2+}$ (25 μM), the proportion of >0.65μ rat peptide particles increased only slightly, however the proportion of >0.65μ human peptide particles dramatically increased, recruiting 82% of the available peptide. Interestingly, the proportions of >0.1μ and >0.22μ particles formed from the human Aβ$_{1-40}$ also increased by 50 and 55%, respectively, following incubation with Zn$^{2+}$, however, the same reaction induced only a 20% and 30% increase, respectively, in the amounts of these particles assembled from rat peptide. Remarkably, only 4% of the human Aβ$_{1-40}$ incubated with Zn$^{2+}$ remained in solution following 0.1μ filtration. Collectively, these data indicate that the human species of Aβ$_{1-40}$ differs from the rat species both in the extent and size of zinc-induced particle formation.

Figure 7D:
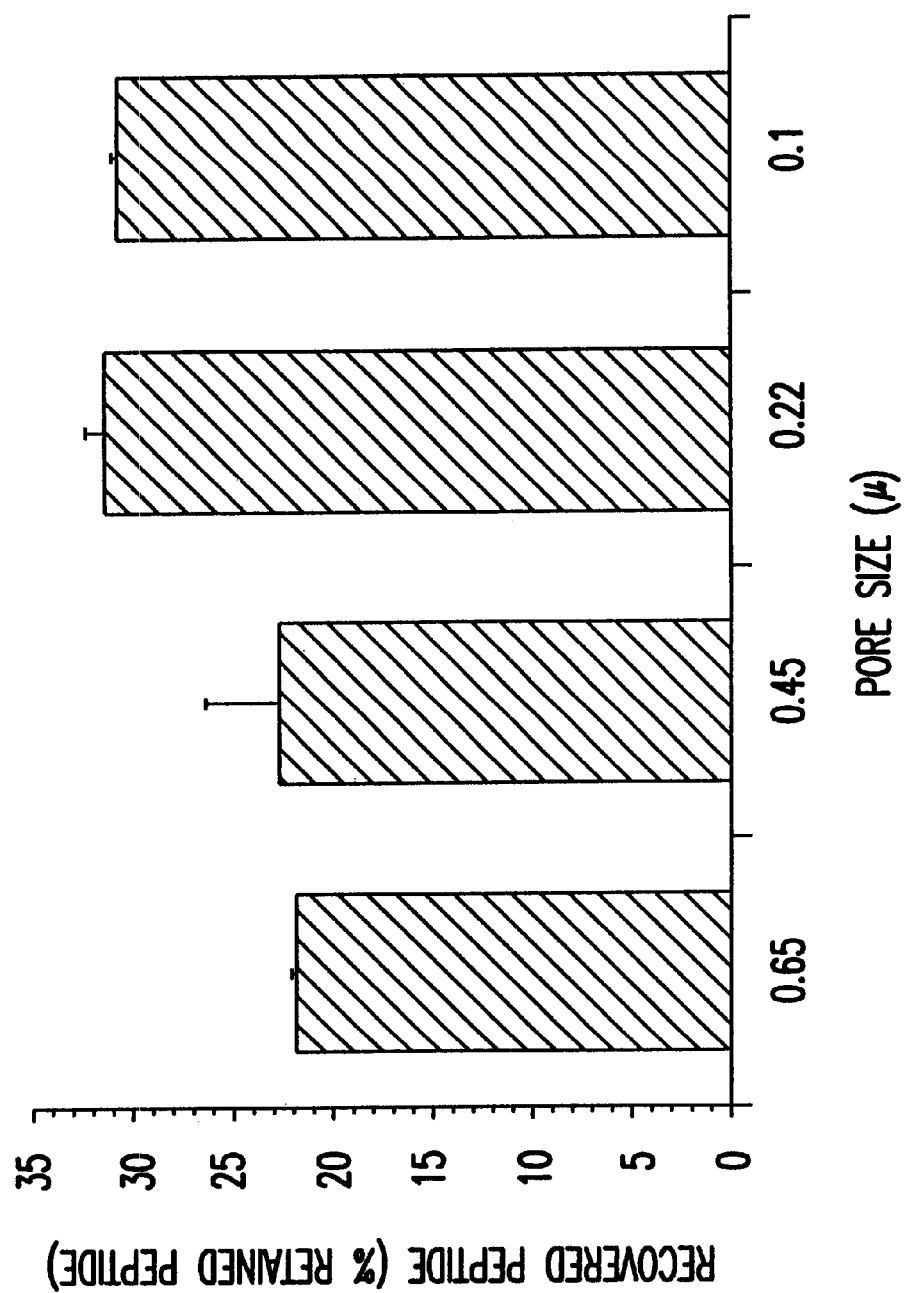

The stoichiometry of zinc:human Aβ in these aggregates is at least 1:1 (FIG. 7c), but increases to 1.3:1 with the smaller (0.1μ) pore size filters. Because the stoichiometries for high- and low- affinity Zn:Aβ binding are ≈1:1 and ≈2:1 respectively, these data indicate that formation of >0.65μ Aβ aggregates is mediated by high-affinity zinc interaction, whereas low-affinity zinc interaction most likely contributes to the formation of smaller (<0.22μ) aggregates. Interestingly, when the retained aggregates are washed with EDTA, only 22% of the peptide is recovered from >0.65 aggregates, although the complexed zinc (using $^{65}$Zn as tracer) is completely recovered (FIG. 7d). This indicates that zinc-induced Aβ aggregation is largely irreversible by chelation. The amount of <0.22μ peptide resolubilized by EDTA treatment is 7% greater, which may reflect the increased contribution of low-affinity zinc binding to the smaller, chelation-reversible, Aβ particle formation.

Sedimentation of zinc-induced Aβ particles by centrifugation resulted in an abundant precipitate of human Aβ$_{1-40}$ which stained with Congo Red (FIG. 8a) and manifested green birefringence under polarized light (FIG. 8b), meeting the criteria for tinctorial amyloid formation. However, following incubation with Zn$^{2+}$ under the same conditions, the rat peptide formed significantly fewer and smaller particles, with minimal birefringence. No rat Aβ amyloid was induced by Zn$^{2+}$ concentrations of less than 10 μM, whereas, by tinctorial criteria, human Aβ amyloid was induced by Zn$^{2+}$ concentrations as low as 3 μM. In neither case was Congo Red-stained material detected following incubation with EDTA-containing buffer.

Taken together, these data indicate that soluble human Aβ$_{1-40}$ has a dramatically greater propensity than rat Aβ$_{1-40}$ to form amyloid in the presence of physiological zinc concentrations. The tinctorial amyloid aggregates are frequently as large as the amorphous amyloid plaque cores purified from AD brain tissue (C. L. Masters et al., *Proc. Natl. Acad. Sci. USA* 82:4245 (1985)). Meanwhile, the small degree (10–20%) of >0.2μ Aβ$_{1-40}$ particle assembly observed following the incubation of Aβ$_{1-40}$ with EDTA probably reflects the relatively slow aggregation which occurs in the presence of neutral pH (S. Tomski and R. M. Murphy, *Arch. Biochem. Biophys.* 294:630 (1992)) and NaCl (C. Hilbich, B. Kisters-Woike, J. Reed, C. L. Masters, K. Beyreuther, *J. Mol. Biol.* 218:149 (1991)). Hence, the specific vulnerability of human Aβ to zinc-induced amyloid formation is a promising explanation for aspects of the pathology of AD and related pathological conditions.

The cerebral cortex, and especially the hippocampus, contains the highest concentrations of zinc in the body (C. J. Frederickson, M. A. Klitenick, W. I. Manton, J. B. Kirkpatrick, *Brain Res.* 273:335 (1983)), and is exposed to extreme fluctuations of extracellular zinc levels (0.15 to 300 μM, C. J. Frederickson, *Int. Rev. Neurobiol.* 31:145 (1989)), e.g. during synaptic transmission (S. Y. Assaf and S.-H. Chung, *Nature* 308:734 (1984); G. A. Howell, M. G. Welch, C. J. Frederickson, *Nature* 308:736 (1984)). The cortical vasculature contains an intraluminal zinc concentration of 20 μM (I. J. T. Davies, M. Musa, T. L. Dormandy, *J. Clin. Pathol.* 21:359 (1968)), but the perivascular interstitial zinc concentration is 0.15 μM (C. J. Frederickson, *Int. Rev. Neurobiol.* 31:145 (1989)). Both sites of high zinc concentration gradients are severely and consistently affected by the pathological lesions of AD (B. T. Hyman, G. W. Van Hoesen, L. J. Kroner, A. R. Damasio, *Ann. Neurol.* 20:472 (1986); G. G. Glenner and C. W. Wong, *Biochem. Biophys. Res. Commun.* 120:885 (1984)). Interestingly, a prominent neurochemical deficit in AD is cholinergic deafferentation of the hippocampus, which raises the concentration of zinc in this region (G. R. Stewart, C. J. Frederickson, G. A. Howell, F. H. Gage, *Brain Res.* 290:43 (1984)). Additional evidence for altered cerebral zinc metabolism in AD include decreased temporal lobe zinc levels (D. Wenstrup, W. D. Ehmann, W. R. Markesbery, *Brain Res.* 533:125 (1990); J. Constantinidis, *Encephale* 16:231 (1990); F. M. Corrigan, G. P. Reynolds, N. I. Ward, *Biometals* 6:149 (1993)), elevated (80%) CSF levels (C. O. Hershey et al., *Neurology* 33:1350 (1983)), an increase in extracellular Zn$^{2+}$-metalloproteinase activities in AD hippocampus (J. R. Backstrom, C. A. Miller, Z. A. Tökés, *J. Neurochem.* 58:983 (1992)), and decreased levels of astrocytic growth-inhibitory factor, a metallothionein-like protein which chelates zinc (Y. Uchida, K. Takio, K. Titani, Y. Ihara, M. Tomonaga, *Neuron* 7:337 (1991)). Recently, a clinical study assayed the effects of oral zinc supplementation (6.7-fold the recommended daily allowance, a dose commonly found in nutritional supplements) upon cognition and plasma APP levels in AD subjects and age-matched controls. Five sequentially-studied AD subjects each experienced an acute decline in cognition within forty-eight hours of ingesting the zinc dose. Under the same conditions, age-matched control subjects remained unaffected by the dose. Among the abnormal changes of neuropsychological measurements taken of the AD group was a 31% drop in Mini-Mental State Examination (M. F. Folstein, S. E. Folstein, P. R. McHugh, *J. Psychiatr. Res.* 12:189 (1975)) scores, after four days of zinc supplementation. This represented a deterioration which, in the ordinary course of the disease, would only be expected after two to four years (Galasko et al., *JAGS* 39:932 (1991)). Plasma APP levels also rose significantly in response to zinc in both the AD and the control groups. All changes were rapidly reversible following cessation of the four day supplementation. Collectively, these reports indicate that there may be an abnormality in the uptake or distribution of zinc in the AD brain. Pervasive abnormalities of zinc metabolism, and premature AD pathology, are also common clinical complications of Down's syndrome (C. Franceschi et al., *J. Ment. Defic. Res.* 32:169 (1988); B. Rumble et al., *N. Engl. J. Med.* 320:1446 (1989)).

The data presented here indicate that stability in the presence of physiological concentrations of zinc clearly differentiates the propensity of human and rat $A\beta_{1-40}$ peptide species to form amyloid. The rapid induction of tinctorial human $A\beta$ amyloid, under physiologically relevant conditions, at peptide concentrations more than an order of magnitude lower than the lowest levels achieved previously for $A\beta_{1-40}$ aggregation (in order to achieve time point measurements of less than 1 minute, the procedure was modified so that samples were centrifuged at 2500 g, allowing the sample volume to be completely filtered in 40 seconds), and within two minutes of incubation, establishes a novel assay system for the study of $A\beta$ amyloidosis. More importantly, these findings can have profound implications for the potential role of zinc in Alzheimer-associated neuropathogenesis.

The following examples are provided by way of illustration to further describe certain preferred embodiments of the invention, and are not intended to be limiting of the present invention, unless specified.

EXAMPLES

Experimental Procedures

Unless otherwise indicated, the following experimental procedures, materials, and reagents were used in the present invention:

Reagents—Precautions taken to avoid zinc contamination included using analytical-grade reagents, electrophoresis-grade Tris-HCl (Bio-Rad), and highly deionized water. $A\beta_{1-17}$ was synthesized by the Biopolymers Laboratory, MIT. $A\beta_{1-40}$ (reverse peptide) was purchased from Bachem (Torrance, Calfi.). Other reagents were from Sigma. $A\beta_{1-40}$ and $A\beta_{1-28}$ results were replicated with peptides from Bachem and Sigma. $A\beta_{1-40}$ results were also replicable with peptide synthesized by W. M. Keck Foundation Biotechnology Resource Laboratory, Yale University. $^{65}$Zn was purchased from Amersham Corp.

$^{65}$Zn$^{2+}$ Binding Studies—Dissolved peptides (1.2 nMol, unless otherwise stated) were dot-blotted onto 0.2-$\mu$m polyvinylidene difluoride membrane (Pierce Chemical Co.), washed twice with chelating buffer (200 $\mu$l×100 mM NaCl, 20 mM Tris-HCl, 1 mM EDTA, pH 7.4), then five times with blocking buffer (200 $\mu$l×100 mM NaCl, 20 mM Tris-HCl, 1 mM MnCl$_2$, pH 7.4), and then incubated (60 min, 20° C.) with $^{65}$Zn (unless otherwise stated 130,000 cpm, 74 mM $^{65}$ZnCl$_2$ in 200 $\mu$l of blocking buffer±competing metal ion chloride). The dot-blot was then washed with blocking buffer (5×200 $\mu$l), the dot excised, placed in a test tube, and assayed by $\gamma$-counting (11% efficiency). The equilibration volume for stoichiometry estimates was regarded as 6×200 $\mu$l. The 214 nm UV absorbance of the unbound flow-through was assayed to determine the total amount of peptide remaining bound onto the membrane. Peptide stock concentrations were confirmed by amino acid analysis. To alter the pH, the $^{65}$Zn incubation was carried out in the presence of 100 mM buffer: MOPS (pH 6.5–7.0), MES (pH 5.0–6.0), acetate (pH 3.5–4.5). The dot-blot apparatus was washed with detergent and EDTA (50 mM) then rinsed and siliconized between use.

$A\beta$ Chromatography—$A\beta$ (55 $\mu$g) was incubated with metal salt solution or EDTA in siliconized 1.5-ml plastic reaction vessels in 100 mM NaCl, 20 mM Tris-HCl, pH 7.4 ("TBS," 100 $\mu$l, 1 h, 37° C.). $A\beta$ was stored in aliquots of 0.52 mg/ml in water at −20° C., then kept at 4° C. when thawed. Reagents were mixed without vortex mixing. The incubated $A\beta$ was directly applied to a G50 SF (Pharmacia, Uppsala, Sweden) column (Bio-Rad Econo-Column, 30×0.7 cm) pre-equilibrated with metal salt solution or EDTA (50 $\mu$M) in TBS at 20° C. and eluted at 8 ml/h (Wiz peristaltic pump, Isco, Lincoln, Nebr.). Absorbance was measured at 254 and 214 nm (Type 6 optical unit, Isco). The amount of $A\beta$ eluting at various peaks was estimated from the area under the curve. This was possible because the relationship of UV absorbance was determined to be linear over the range of $A\beta$ dilutions used in these studies, indicating that absorbance is proportional to the amount of peptide present despite polymerization state (see below). The maximum recovery of $A\beta$ occurs in the presence of EDTA. Because the sample eluted in a volume of approximately 15 ml, the average concentration of the peptide on the column was 0.8 $\mu$M.

To study the effects of protein blocking upon adsorption of $A\beta$ to the chromatography column, a Sephadex G50 SF column which had been characterized previously for $A\beta$ behavior was eluted with 3% bovine serum albumin (BSA) in TBS (50 ml) and equilibrated with non-BSA-containing buffer, subsequent to repeating the $A\beta$ experiments.

Spectroscopic Assay--Measurements were performed on a Hewlett-Packard 8452A diode array spectrophotometer using a 1-cm path length quartz cuvette. Concentration versus absorbance curves were performed at 214 nm, 254 nm, 280 nm, and full spectrum. 214 nm readings were 50-fold more sensitive in detecting the peptide than 254 nm readings, whereas the 280 nm readings of low micromolar $A\beta$ solutions were below sensitivity limits and hence could not be used in these studies. The standard curves generated were linear at concentrations below 0.1 mg/ml. In addition, the effects of Cu$^{2+}$, Zn$^{2+}$, EDTA, and TBS upon absorbance were examined. At concentrations below 0.1 mg/ml, adjusting the peptide in water to TBS caused 15% quenching. Cu$^{2+}$—, Zn$^{2+}$—, and EDTA-containing $A\beta$ solutions were studied for artifactual absorbance over the linear range of the 214 nm absorbance curve. 1 mM EDTA caused 60% quenching, hence 50 $\mu$M EDTA was employed, contributing a similar degree of quenching to that observed with Cu$^{2+}$ and Zn$^{2+}$.

$A\beta$ Binding to Kaolin (Aluminum Silicate)—Kaolin suspension was prepared in high performance liquid chromatography water (Fisher), defined, and adjusted to 50% (v/v). $A\beta$ (40 $\mu$g) was incubated in siliconized reaction vessels with either kaolin or Sephadex G50 SF (10 $\mu$l×50% (v/v)) in Cu$^{2+}$, Zn$^{2+}$, or EDTA (100 $\mu$l in TBS, 5 min, room temperature). The suspension was then pelleted (1500×g, 3 min) and the supernatant removed and diluted 20-fold with water to bring the UV absorbance readings into the linear range. Samples were assayed at 214 nm before and after incubation with kaolin or Sephadex.

Tryptic Digestion of $A\beta$-$A\beta_{1-40}$ (13.9 $\mu$g) was incubated with Zn$^{2+}$ (12 $\mu$l in blocking buffer, 1 h, 37° C.) and then digested with trypsin (12 ng, 3 h, 37° C.). The reaction was stopped by adding SDS sample buffer containing phenylmethylsulfonyl fluoride (1 mM), boiling the samples (5 min), and applying the samples to Tris/Tricine gel electrophoresis and transfer. The blot was washed with EDTA, Coomassie-stained, incubated with $^{65}Zn^{2+}$, individual bands were excised, assayed for $^{65}Zn^{2+}$ binding, and N-terminal sequenced to confirm the identity of the digestion products. The effects of $Zn^{2+}$ (up to 100 µM in TBS) on the activity of trypsin, itself, were assayed by assay of Z-Arg-amido-4-methylcoumarin (Sigma) fluorescent cleavage product and determined to be negligible. It was found that 200 µM $Zn^{2+}$, however, inhibited tryptic activity by 12%.

Example 1

Analyses of $^{65}Zn^{2+}$ Binding to Aβ

Aliquots of Aβ were incubated (60 min) with $^{65}Zn^{2+}$ in the presence of varying concentrations of unlabeled $Zn^{2+}$ (0.01–50 µM total). The proportion of $^{65}Zn^{2+}$ binding to immobilized peptide (1.0 nmol) described two binding curves as shown in FIG. 1a (Scatchard plot). Values shown are means±S.D., n≧3. The high-affinity binding curve has been corrected by subtracting the low-affinity component, and the low-affinity curve has had the high-affinity component subtracted. (FIG. 1b) depicts specificity of the $Zn^{2+}$ binding site for various metals. Aβ was incubated (60 min) with $^{65}Zn^{2+}$ (157 nM, 138,000 cpm) and competing unlabeled metal ions (50 µM total). (FIG. 1c) depicts $^{65}Zn^{2+}$ (74 nM, 104,000 cpm) binding to negative (aprotinin, insulin α-chain, reverse peptide 40-1) and positive (bovine serum albumin (BSA)) control proteins and Aβ fragments (identified by their residue numbers within the Aβ sequence, gln11 refers to Aβ$_{1-28}$ where residue 11 is glutamine). Percent binding of total counts $^{65}Zn^{2+}$/min added is corrected for the amounts (in nanomoles) of peptides adhering to the membrane. (FIG. 1d) depicts as for 1a, with Aβ$_{1-28}$ peptide substituting for Aβ$_{1-40}$. 157 nM $^{65}Zn$ (138,000 cpm) is used in this experiment to probe immobilized peptide (1.6 nmol). (FIG. 1e) depicts pH dependence of $^6Zn^{2+}$ binding to Aβ$_{1-40}$.

Example 2

Effect of $Zn^{2+}$ and Other Metals on Aβ Polymerization Using G50 Gel Filtration Chromatography Results shown are indicative of n≧3 experiments where 55 µg of Aβ is applied to the column and eluted in 15 ml, monitored by 254 nm absorbance. (FIG. 2a) depicts chromatogram of Aβ in the presence of EDTA, 50 µM, $Zn^{2+}$, 0.4 µM; $Zn^{2+}$, 25 µM; and $Cu^{2+}$, 25 µM. The elution points of molecular mass standards and relative assignments of Aβ peak elutions are indicated. Mass standards were blue dextran (2×10$^6$ kDa, V$_0$=void volume), BSA (66 kDa), carbonic anhydrase (29 kDa), cytochrome c (12.4 kDa), and aprotinin (6.5 kDa). The mass of Aβ is 4.3 kDa. (FIG. 2b) depicts relative amounts (estimated from areas under the curve) of soluble Aβ eluted as monomer, dimer, or polymer in the presence of various metal ions (25 µM), varying concentrations of $Zn^{2+}$ or $Cu^{2+}$ (the likelihood of Tris chelation is indicated by upper limit estimates), and EDTA. Data for experiments performed in the presence of copper were taken from 214 nm readings and corrected for comparison. (FIG. 2c) depicts effects of pre-blocking the chromatography column with BSA upon the recovery of Aβ species in the presence of zinc (25 µM), copper (25 µM), or chelator.

Example 3

Aβ Binding to Kaolin (Aluminum Silicate): Effects of Zinc (25 µM), Copper (25 µM), and EDTA (50 µM)

(FIG. 3a) depicts concentration (by 214 nm absorbance) of Aβ remaining in supernatant after incubation with 10 mg of G50 Sephadex. (FIG. 3b) depicts concentration (by 214 nm absorbance) of Aβ remaining in supernatant after incubation with 10 mg of kaolin, expressed as percent of the starting absorbance.

Example 4

Effect of $Zn^{2+}$ Upon Aβ Resistance to Tryptic Digestion (FIG. 4a) depicts a blot of tryptic digests of Aβ (13.9 µg) after incubation with increasing concentrations of zinc (lane labels, in micromolar), stained by Coomassie Blue. Digestion products of 3.6 kDa (Aβ$_{6-40}$), and 2.1 kDa (Aβ$_{17-40}$), as well as undigested Aβ$_{1-40}$ (4.3 kDa), are indicated on the left. The migration of the low molecular size markers (STD) are indicated (in kilodaltons) on the right. (FIG. 4b) depicts $^{65}Zn^{2+}$ binding to Aβ tryptic digestion products. The blot in 4a was incubated with $^{65}Zn^{2+}$, the visible bands excised, and the bound counts for each band determined. These data are typical of n=3 replicated experiments.

To determine whether Aβ binds zinc, a synthetic peptide representing secreted Aβ$_{1-40}$ was incubated with $^{65}Zn^{2+}$. Rapid binding (60% B$_{max}$ at 1 min), which plateaued at 1 h, was observed. Scatchard analysis of $^{65}Zn^{2+}$ binding describes two saturable binding curves, a high affinity curve (K$_a$<107 nM), and a lower affinity curve (K$_a$<5.2 µM) (FIG. 1a). The affinity constant estimates might be skewed by assuming that the Tris buffer does not bind zinc. In fact, Tris-HCl binds zinc and copper with stability constants of 4.0 and 2.6, respectively (Dawson et al., *Data for Biochemical Research*, Oxford University Press (1986)). Incubating Aβ in the presence of higher concentrations of Tris (150 and 500 mM) abolishes $^{65}Zn^{2+}$ binding to Aβ (≈50% and ≈95%, respectively), indicating that Tris-induced $Zn^{2+}$ chelation cannot be excluded. Our calculated affinity constants are therefore upper limit estimates.

Figure 1C:
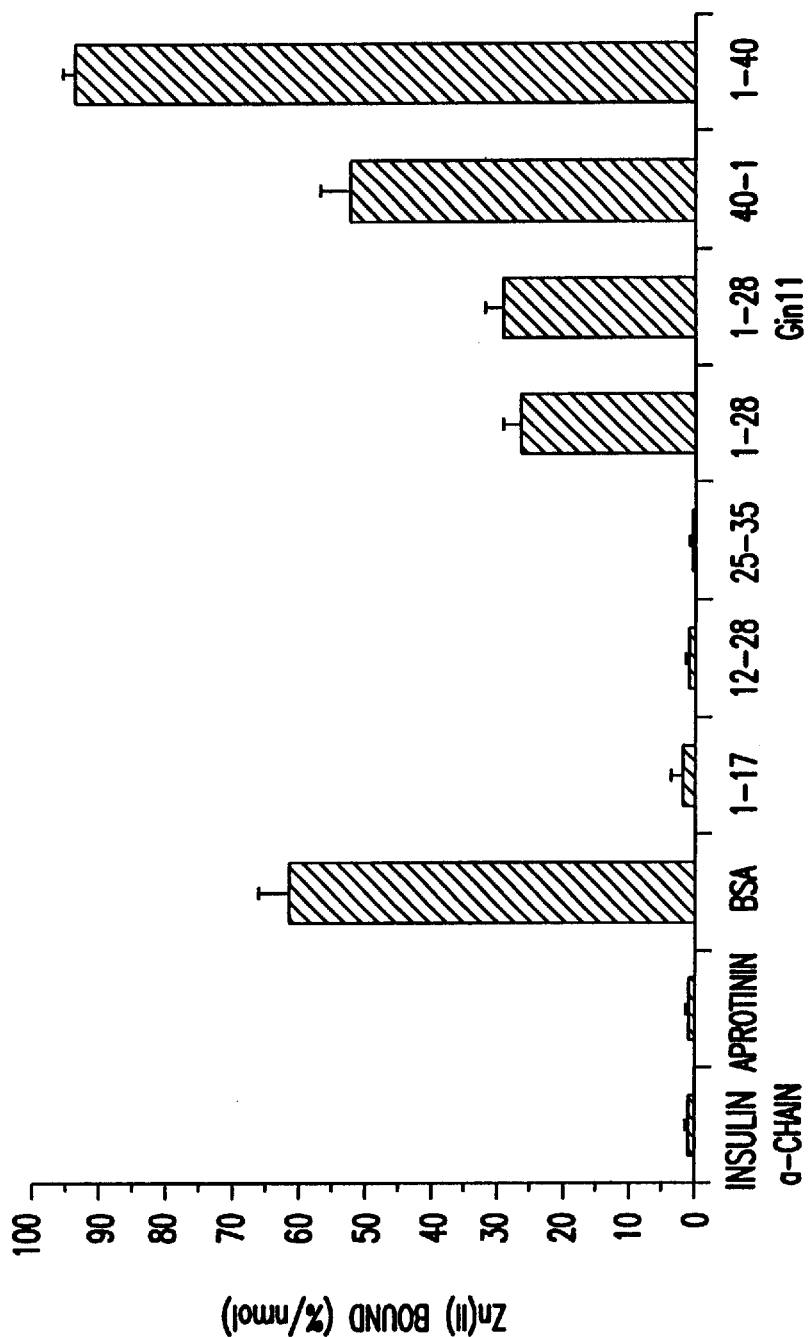
Figure 1D:
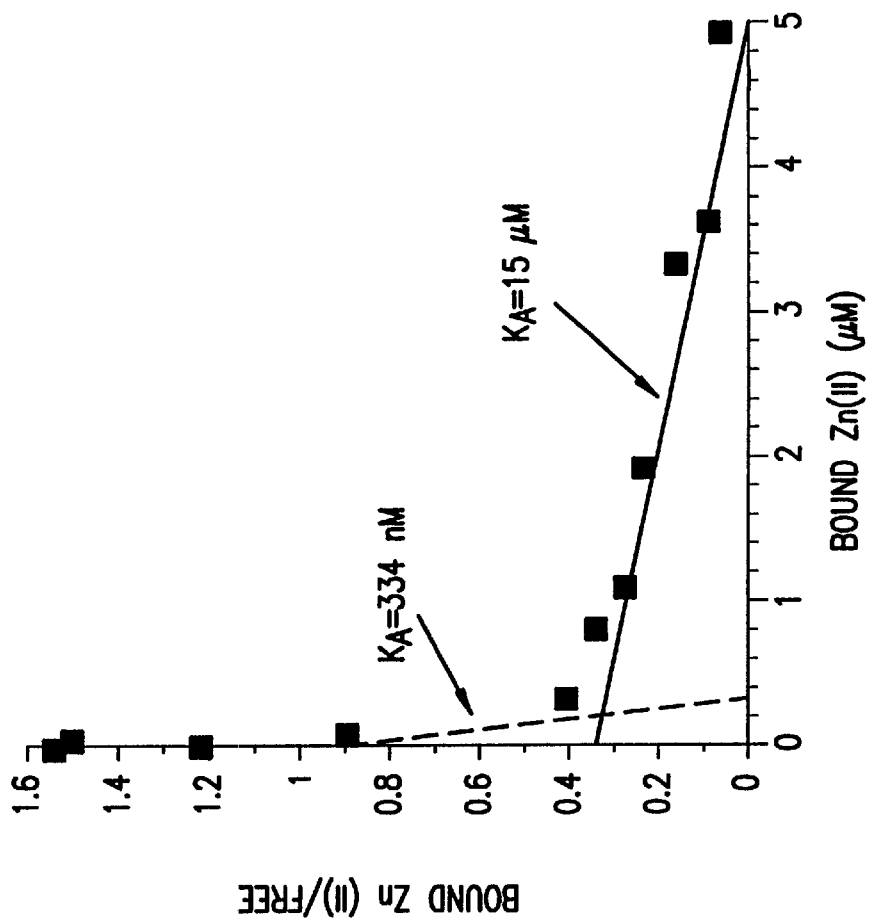
Figure 1E:
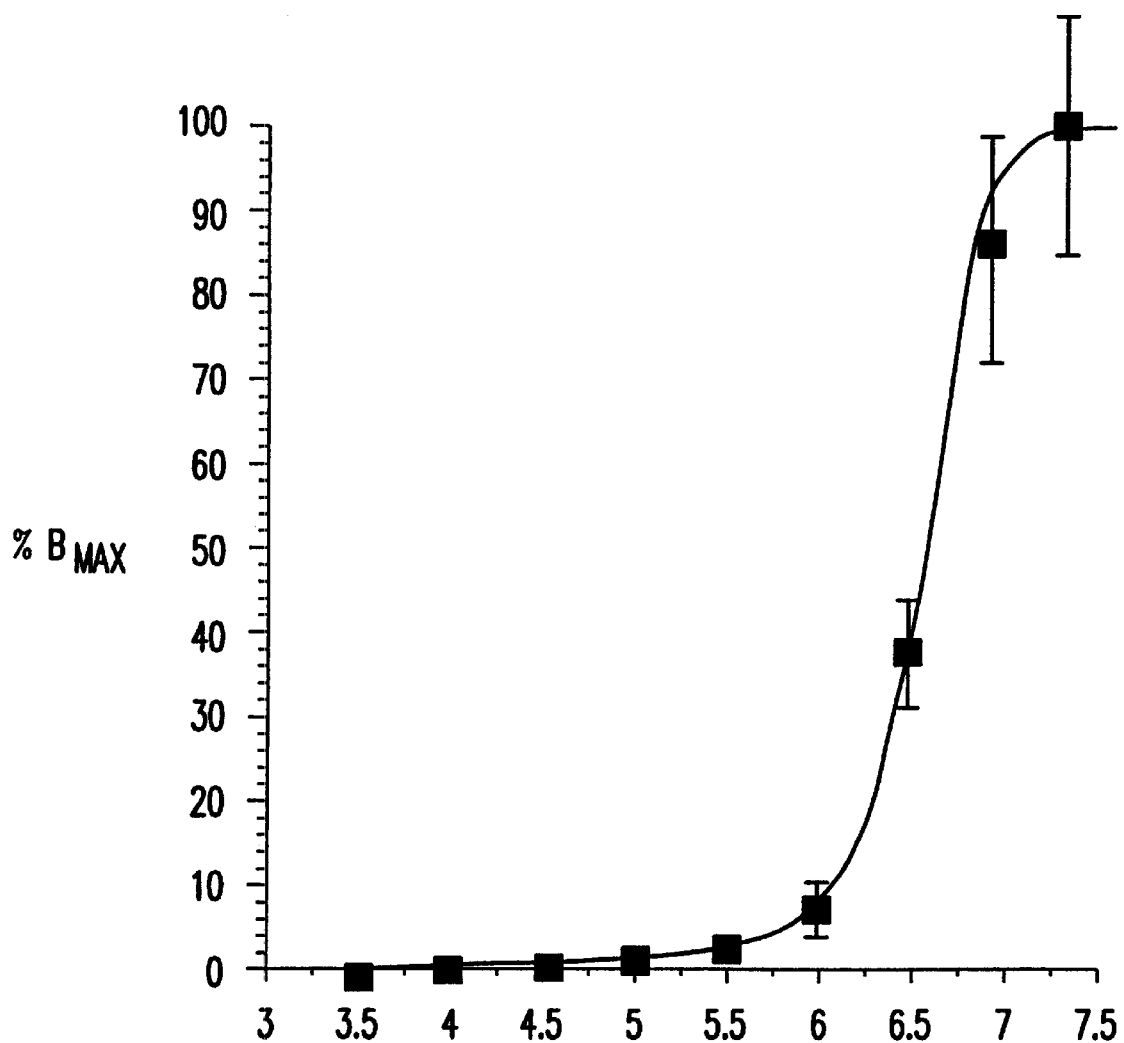

$^{65}Zn^{2+}$ binding is very specific, with $Zn^{2+}$ being the only unlabeled metal ion tested that is capable of competing off the label (FIG. 1b). To determine the specific region of Aβ involved in zinc binding and to validate the dot-blot binding system, equivalent amounts of various peptides representing fragments of Aβ$_{1-40}$ and peptide controls were assayed for $^{65}Zn^{2+}$ binding in this system (FIGS. 1c and 1d).

The reverse sequence (40-1) control peptide only binds 50% of B$_{max}$ compared with Aβ$_{1-40}$ (FIG. 1c), indicating that zinc binding is not merely a consequence of the presence of favorable residues. Aβ$_{1-28}$ bound 30% of B$_{max}$, indicating that the carboxyl terminus plays an important role in promoting zinc binding. Glutamine substitution for the glutamate at position 11 of Aβ$_{1-28}$, in accordance with the Down's syndrome Aβ sequence reported by Glenner and Wong, *Biochem. Biophys. Res. Commun.* 120:885–890 (1984), does not interfere with $^{65}Zn^{2+}$ binding. The Scatchard plot of $^{65}Zn^{2+}$ binding to Aβ$_{1-28}$ reveals similar lower affinity (K$_a$<15 µM) and higher affinity (K$_a$<334 nm) binding associations (FIG. 1d) to those of Aβ$_{1-40}$, but overall the Aβ$_{1-28}$ peptide binds zinc less avidly. Although the Aβ$_{1-28}$ peptide clearly binds zinc, peptides overlapping this region (1-17 and 12-28) do not individually bind zinc. Additionally, a peptide covering a region of the carboxyl terminus (25–35) also is unable to bind zinc (FIG. 1c).

The calculated stoichiometry of high-affinity $Zn^{2+}$-binding to Aβ, derived from the x-intercepts on the Scatchard plots (FIG. 1, a and d), is 0.7:1 (Aβ$_{1-40}$) and 1:4 (Aβ$_{1-40}$). For low-affinity binding, the $Zn^{2+}$:Aβ ratio is 2.5:1 (Aβ$_{1-40}$) and 4:1 (Aβ$_{1-28}$).

$^{65}Zn^{2+}$ binding of sequenced tryptic digest products of Aβ (FIG. 4b) indicates that the 6-40 fragment binds zinc, but that the other visible digest fragment 17-40 (FIG. 4b), representing the post-secretase (Esch et al., *Science* 248:1122–1124 (1990); Sisodia et al., *Science* 248:492–495 (1990)) carboxyl-terminal product, does not bind zinc. The contribution of histidines (residues 6, 13, and 14) to $Zn^{2+}$ binding is indicated by the deterioration of binding with lower pH (30% of $B_{max}$ at pH 6.0, FIG. 1e). Taken together, these data indicate that zinc coordination requires the contiguous sequence between residues 6 and 28, a region containing all 3 histidine residues, but optimal zinc binding also requires the presence of the carboxyl-terminal domain.

Figure 2A:
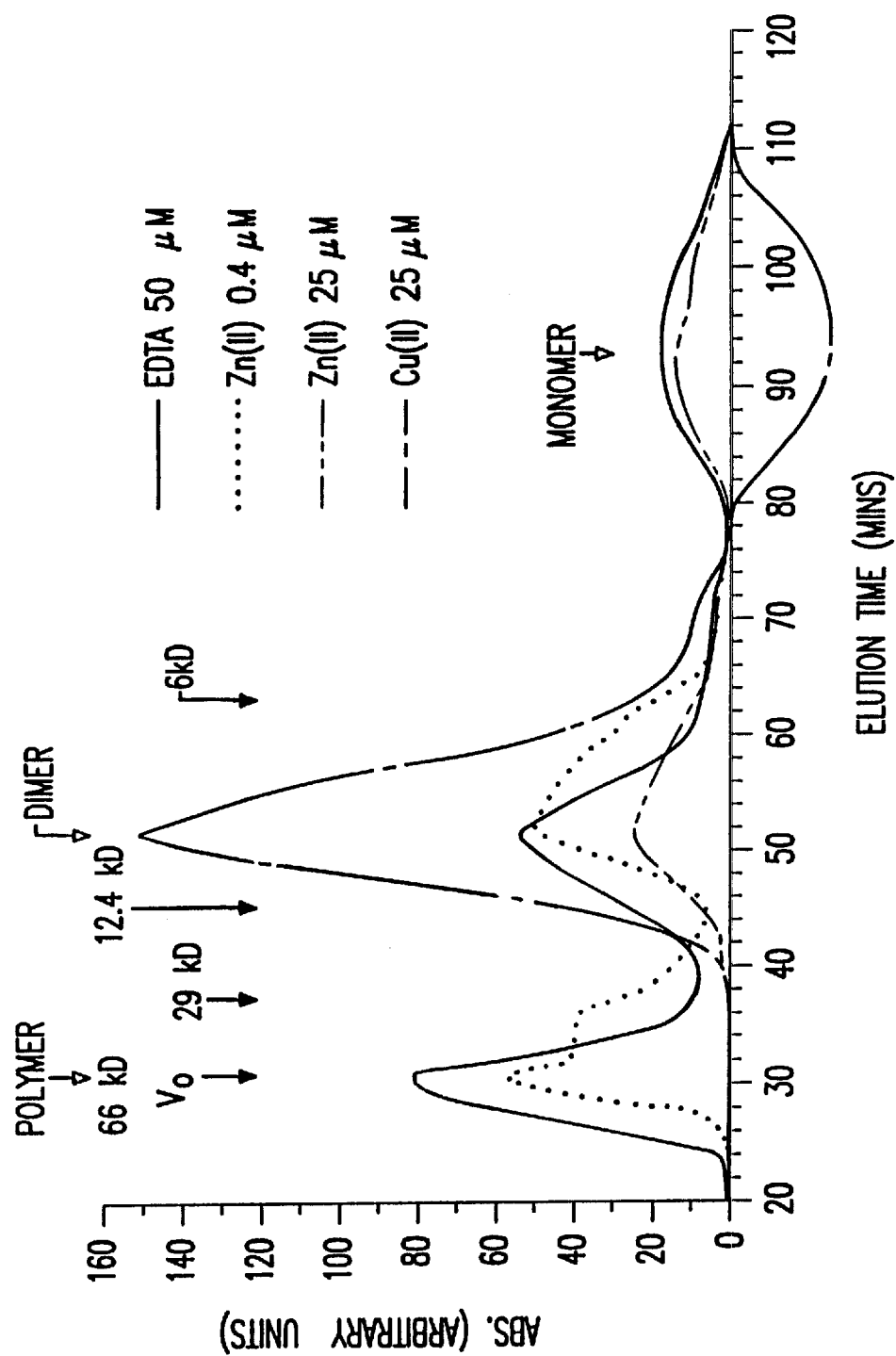
FIGS. 2a, 2b and 2c. Effect of $Zn^{2+}$ and other metals on Aβ polymerization using G50 gel filtration chromatography.
Figure 2B:
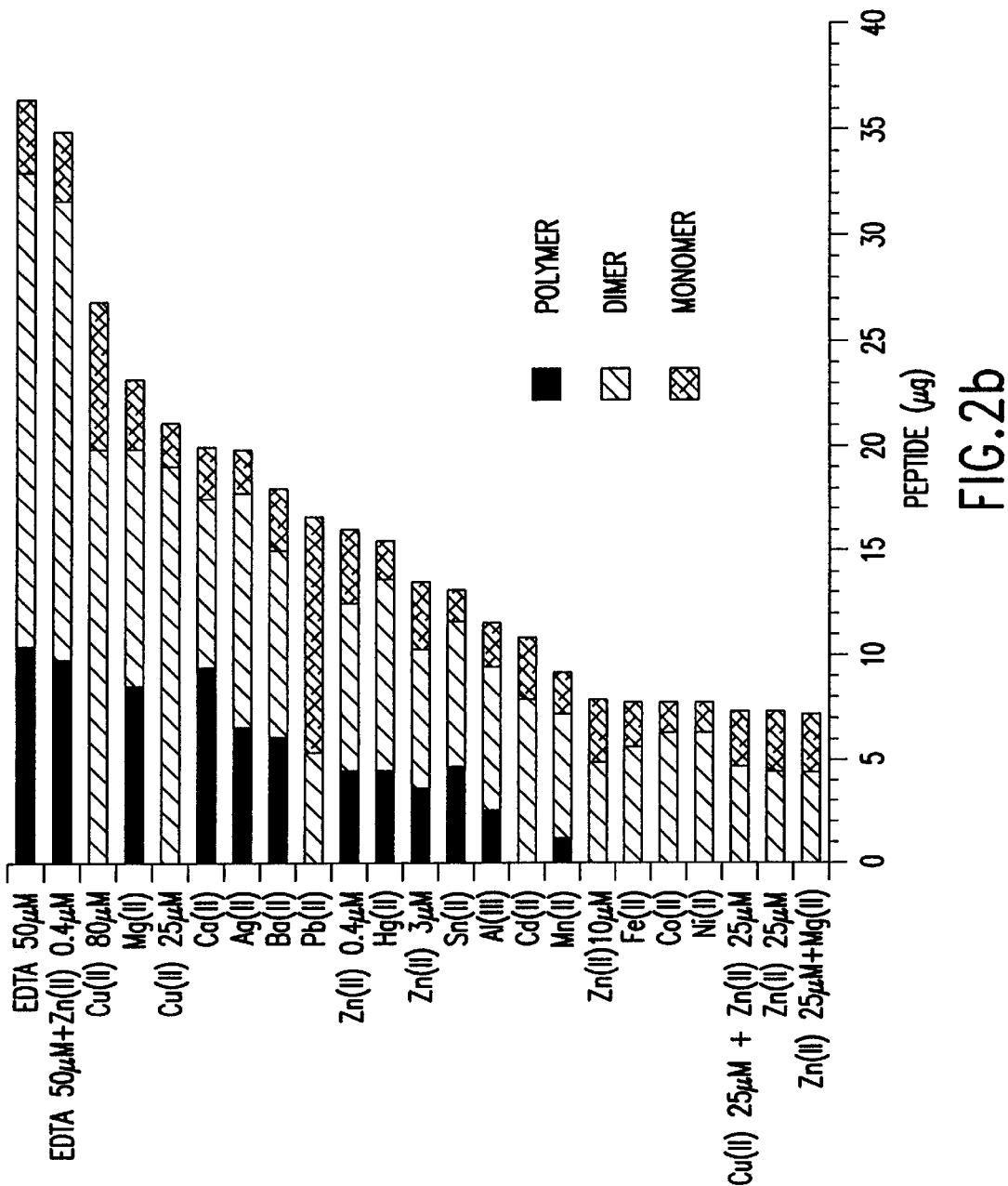

Next, it was tested whether zinc binding could affect Aβ conformation as assayed by migration upon gel-filtration chromatography. Major Aβ species believed to correspond to monomeric, dimeric, and polymeric forms were observed (FIG. 2a). Total concentrations of $Zn^{2+}$ as low as 0.4 μM decrease recoverable Aβ eluting from the column when compared with the elution profile obtained in the presence of EDTA and other metals (FIGS. 2a and 2b). At 25 μM total $Zn^{2+}$, <20% of the Aβ elutes. This deficit mainly affects the high order polymer and dimeric species which apparently do not enter the gel. Meanwhile, the relative amount of monomeric Aβ is preserved. A systematic assessment of several metals indicates that the reduction of Aβ recoverable by chromatography is most sensitive to $Zn^{2+}$, with related transition metals $Co^{2+}$, $Ni^{2+}$, and $Fe^{2+}$ (at 25 μM) displaying similar effects on chromatography to those obtained with only 10 μM $Zn^{2+}$ (FIG. 2b). Other transition metals, heavy metals, and $Al^{3+}$ (25 μM) have partial effects on Aβ solubility comparable with 3 μM total $Zn^{2+}$. Meanwhile, $Ba^{2+}$, $Ag^{2+}$, $Mg^{2+}$, and $Ca^{2+}$ (25 μM) have the least effect on Aβ compared with the EDTA profile, although 40% less total peptide appears to elute. $Pb^{2+}$ (25 μM) most strongly promotes the elution of the monomeric peptide, abolishing high order polymers; overall recovery is similar to that obtained with 0.4 μM total $Zn^{2+}$. In making comparisons of the effects of these metal ions, it is again important to consider the differential metal ion chelating effects of Tris mentioned earlier.

A dramatic increase in Aβ dimerization is observed with $Cu^{2+}$ (25 μM total). This metal also induces exaggerated Aβ absorbance (4-fold) at 254 nm when compared with 214 nm absorbance and induces the monomeric species to apparently fluoresce at 254 nm causing negative readings (FIG. 2a) which are proportionally positive at 214 nm (FIG. 2b). A higher concentration of $Cu^{2+}$ (80 μM total) promotes increased recovery of Aβ, indicating that the presence of $Cu^{2+}$ favors solubility in this system.

The metal ions which most favored Aβ solubility ($Mg^{2+}$, 25 μM and total $Cu^{2+}$, 25 μM) were tested for their ability to stabilize Aβ in a soluble state in the presence of 25 μM total $Zn^{2+}$. These combinations neither rescue nor worsen $Zn^{2+}$-induced loss of Aβ recovery (FIG. 2b). Overall, these data suggest that $Zn^{2+}$ binding reduces the recovery of Aβ, whereas a chelating agent attenuates this effect.

Figure 2C:
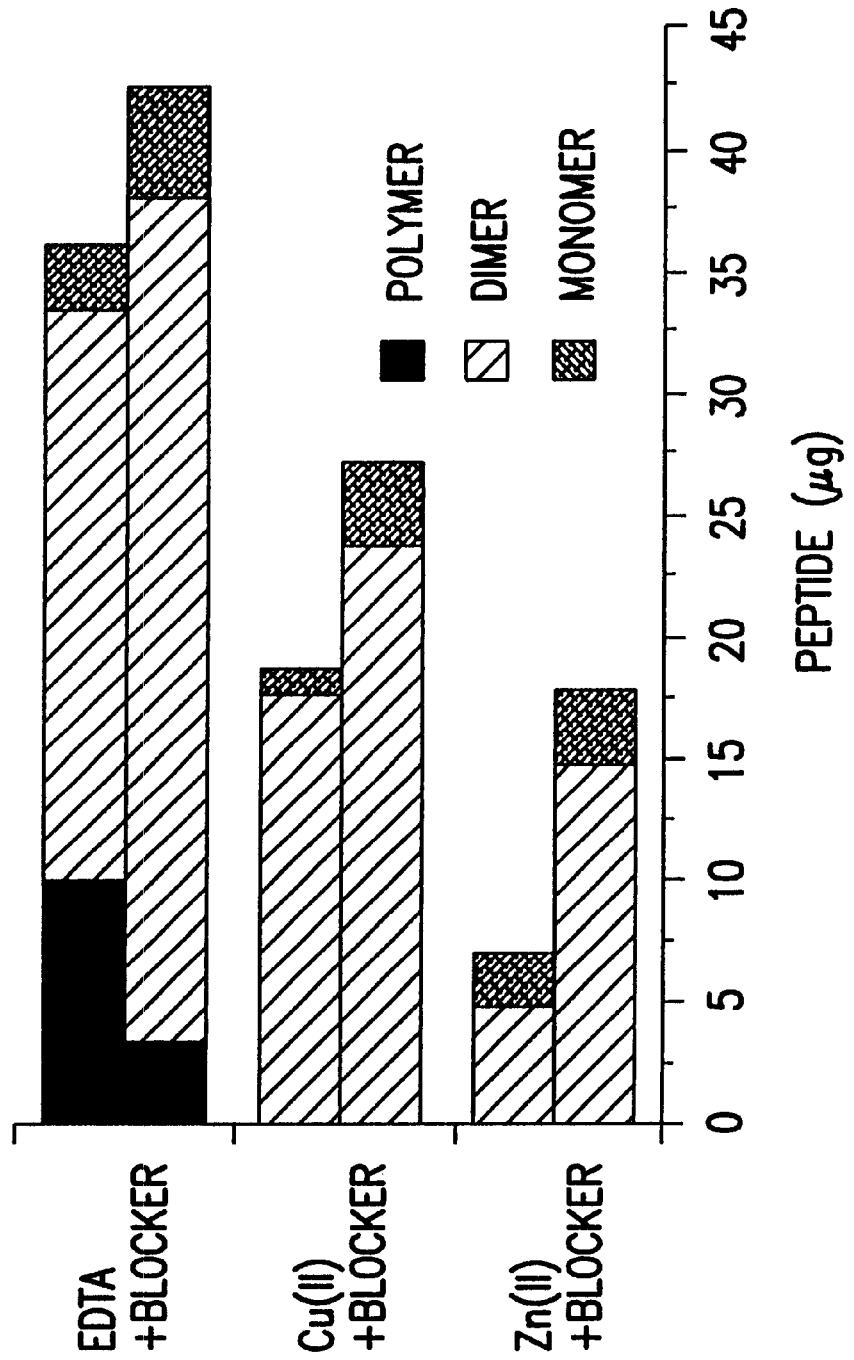

To determine whether the zinc-induced loss of Aβ during chromatography occurs because of Aβ precipitation onto a surface of the apparatus, it was attempted to block the effect. Pretreating the column with 3% BSA as an adsorption blocker significantly increases the amounts of Aβ recovered from the column, indicating that the peptide precipitates onto a column component (FIG. 2c). Blocking the column results in a 200% increase in the recovery of Aβ in the presence of $Zn^{2+}$ (25 μM total), a 75% increase in recovery in the presence of $Cu^{2+}$ (25 μM total), but only a 10% increase in the presence of EDTA (50 μM). This confirms that precipitation onto the column is most specifically accelerated by zinc.

To determine the part of the column onto which Aβ was precipitating, Aβ solutions were incubated with various column components and assayed Aβ concentrations by UV absorption before and after the incubation. Replicating the chromatography experimental conditions, Aβ (100 μM in equilibration buffer) was incubated for 1 h in plastic reaction vessels with or without the presence of Sephadex. Loss to the plastic accounts for <5% of the observed precipitation, to siliconized plastic <1%, and binding to Sephadex <1%. Hence, Aβ precipitates are unlikely to be adsorbing to the Sephadex or plastic support. However, similar incubations in borosilicate glass test tubes result in 20% adsorption, which increase to 35% in the presence of zinc (25 Mm).

The glass in the Bio-Rad Econo Columns is made of 7740 Pyrex (Corning, Park Ridge, Ill.) and is composed of $SiO_2$, 80.6%; $B_2O_3$, 13.0%; $Na_2O$, 4.0%; and $Al_2O_3$, 2.3%. Because of reports associating aluminosilicates with β-amyloid deposition (Masters et al., *EMBO J.* 4:2757–2763 (1985a); Candy et al., *Lancet* 1:354–357 (1986)), experiments were carried out to test whether Aβ binds to aluminum silicate. Rapid and extensive binding of Aβ to kaolin, an insoluble hydrated aluminum silicate was observed. Moreover, incubation of Aβ (0.4 mg/ml) with Sephadex (5%, v/v) in the presence of zinc, copper, or EDTA causes only small changes in solubility which may be attributed to binding to the plastic in the reaction vessels (FIG. 3a). Incubation of Aβ (0.4 mg/ml) with kaolin (5%, v/v, 5 min, room temperature), causes precipitation of up to 87% of the peptide present. This precipitation is greatest in the presence of zinc (25 μM) where the amount of Aβ recovered from the zinc incubation supernatant is nearly half of the amount recovered from the EDTA incubation supernatant (FIG. 3b). The effect of copper (25 μM) upon kaolin-induced Aβ precipitation is similar to the effect of EDTA (FIG. 3b). The binding of Aβ to kaolin is not reversible to subsequent treatment with 10 mM EDTA, but can be eluted by 2M NaOH.

To further test whether zinc induces irreversible precipitation of Aβ in the absence of kaolin, Aβ incubated with $Zn^{2+}$ (200 μM, 1–24 h, 20° C.) was subjected to SDS Tris/Tricine gel electrophoresis. The monomeric species was the major band detected on Coomassie-stained gels and migrated identically to unincubated Aβ, indicating that zinc does not induce covalent or SDS-resistant polymerization of Aβ.

Since the APP secretase site at Lys-16 (Esch et al., *Science* 248:1122–1124 (1990); Sisodia et al., *Science* 248:492–495 (1990)) in Aβ is within the obligatory zinc binding region, the ability of $Zn^{2+}$ to protect Aβ from secretase-type cleavage by trypsin, a serine-protease whose activity was found to be unaffected by zinc, was next tested. Amino-terminal sequence on Aβ tryptic digestion products transferred to polyvinylidene difluoride membrane following SDS-polyacrylamide gel electrophoresis indicated two detectable fragments corresponding to residues 6-40 and 17-40 (FIG. 4a). The predicted tryptic cleavage product representing residues 29-40 did not appear on the blot and may not be retained by the polyvinylidene difluoride membrane during transfer and treatment. Digestion is inhibited by the presence of increasing concentrations of $Zn^{2+}$. At 200 μM, $Zn^{2+}$ causes complete inhibition of Aβ hydrolysis; however, at this zinc level, tryptic activity is also slightly inhibited. Probing the blot with $^{65}Zn^{2+}$ confirmed the zinc binding identity of the peptide fragments and facilitated quantification of the hydrolysis of the zinc binding site (FIG. 4b). The rate of digestion of A$\beta_{1-40}$ and the A$\beta_{1-40}$ fragment is inhibited by the presence of zinc, whereas the digestion of the A$\beta_{17-40}$ fragment is not inhibited by increasing zinc concentrations. Hence, only the peptides possessing the intact zinc binding domain of A$\beta$ (residues 6-28), and therefore capable of binding $Zn^{2+}$ (FIG. 4b), have their rates of digestion inhibited by zinc in this experiment. These data indicate that secretase-type cleavage of A$\beta$ can be inhibited by $Zn^{2+}$ binding to the A$\beta$ substrate.

The above data indicate that soluble A$\beta_{1-40}$ possesses high and low affinity zinc binding affinities. The zinc binding site on A$\beta$ maps to residues 6-28, with possibly conformational- and histidine-dependent properties. The affinity constants for zinc binding indicate that both binding associations are within physiological zinc concentrations, but that occupancy of the low affinity binding site may be associated with accelerated precipitation of A$\beta$ by aluminum silicate (kaolin). Occupancy of the high affinity site appears to have little effect on A$\beta$ precipitation and is very highly specific, although the data cannot exclude the possibility of specific binding sites for alternative metals elsewhere on A$\beta$. Copper's strong conformational interaction (dimerization and fluorescence) with A$\beta$ indicates that it may also directly interact with the peptide and may have a role in preventing A$\beta$ precipitation onto aluminum silicate.

Extracellular zinc may play a role in the physiology of APP function by modifying its adhesiveness to extracellular matrix elements (Bush et al., *J. Biol. Chem.* 268:16109–16112 (1993)). This is important because APP may play a role in cell adhesiveness (Shivers et al., *EMBO J.* 7:1365–1370 (1988)) and neurite outgrowth (Milward et al., *Neuron* 9:129–137 (1992)). The physiological function of the A$\beta$-zinc interaction remains unclear, however, increased resistance of A$\beta$ to proteolytic cleavage in the presence of zinc would increase the peptide's biological half-life, and increased adhesiveness may also promote its binding to extracellular matrix elements. It has been reported recently that A$\beta$ promotes neurite outgrowth by complexing with laminin and fibronectin in the extracellular matrix (Koo et al., *Proc. Natl. Acad. Sci. USA* 90:4748–4752 (1993)). Hence, both APP and A$\beta$ may interact with the extracellular matrix to modulate cell adhesion. The possibility that zinc is a local environmental cofactor modulating this interaction merits further investigation.

APP is highly abundant in platelets and brain (Bush et al., *J. Biol. Chem.* 265:15977–15983 (1990)) where zinc is also highly concentrated (Baker et al., *Thromb. Haemostasis* 39:360–365 (1978); Frederickson, C. J., *Int. Rev. Neurobiol.* 31:145–328 (1989)). Although APP is concentrated in vesicles in both of these tissues (Bush et al., *J. Biol. Chem.* 265:15977–15983 (1990); Schubert et al., *Brain Res.* 563:184–194 (1991)), and zinc is actively taken up (Wolf et al., *Neurosci. Lett.* 51:277–280 (1984)) and stored in synaptic vesicles in nerve terminals throughout the telencephalon (Perez-Clausell and Danscher, *Brain Res.* 3371:91–98 (1985), the colocalization of APP with zinc in these vesicles has yet to be demonstrated. Vesicular zinc storage is thought to play a role in stabilizing functional molecules such as NGF and insulin as insoluble intravesicular precipitates (Frederickson et al., *J. Histochem. Cytochem.* 35:579–583 (1987)). Zinc may similarly play a role in stabilizing APP and A$\beta$.

The interaction between A$\beta$ and zinc may be compared with that of insulin, a peptide whose zinc binding properties are well characterized. Like A$\beta$, insulin exhibits histidine-dependent high-affinity ($K_a$=5 $\mu$M) and low-affinity ($K_a$= 140 $\mu$M) zinc binding with stoichiometries of 1:1 (insulin:zinc) and 1:2, respectively (Goldman and Carpenter, *Biochemistry* 13:4566–4574 (1974)). Additionally, metal-free insulin exhibits a pH-dependent polymerization pattern consisting of monomer, dimer, tetramer, hexamer, and higher aggregation states, in dynamic equilibrium. At neutral pH, zinc and other divalent metal ions shift the equilibrium toward the higher aggregation states. At stoichiometric ratios of $Zn^{2+}$:insulin in excess of 0.33, the peptide precipitates (Fredericq, E., *Arch. Biochem. Biophys.* 65:218–228 (1956)), reminiscent of zinc's effects upon A$\beta$ observed in the current studies.

A$\beta$ chelates zinc with such high affinity that reports of its neurotoxic effects in neuronal cultures (Yankner et al., *Science* 250:279–282 (1990); Koh et al., *Brain Res.* 533:315–320 (1990)) might be explained by a disturbance of zinc homeostasis. A$\beta$ accumulates most consistently in the hippocampus, where extreme fluctuations of zinc concentrations occur (0.15–300 $\mu$M) (Frederickson, C. J., *Int. Rev. Neurobiol.* 31:145–328 (1989)), e.g., during synaptic transmission (Assaf and Chung, *Nature* 308:734–736 (1984); Howell et al., *Nature* 308:736–738 (1984); Xie and Smart, *Nature* 349:521–524 (1991)). Choi and co-workers (Weiss et al., *Nature* 338:212 (1989)) have proposed that this transsynaptic movement of zinc may have a normal signaling function and may be involved in long term potentiation. The hippocampus is the region of the brain that both contains the highest zinc concentrations (Frederickson et al., *Brain Res.* 273:335–339 (1983)) and is most severely and consistently affected by the pathological lesions of Alzheimer's disease (Hyman et al., *Ann. Neurol.* 20:472–481 (1986)). One of the prominent neurochemical deficits in Alzheimer's disease is cholinergic deafferentation of the hippocampus, which has been shown to raise the concentration of zinc in this region (Stewart et al., *Brain Res.* 290:43–51 (1984)).

The rapid zinc-accelerated precipitation of A$\beta$ by aluminum silicate (kaolin) is significant because of the candidacy of aluminum as a pathogenic agent in AD (Perl and Brody, *Science* 208:297–299 (1980)). Recent reports of $Zn^{2+}$- and $Al^{3+}$-induced sedimentation of A$\beta$ (Mantyh et al., *J. Neurochem.* 61:1171–1174 (1993)), and the nucleation of A$\beta$ precipitation by aluminosilicate (Candy et al., *Biochem. Soc. Trans.* 21:53S (Abstract) (1992)) also support these observations.

Evidence for altered zinc metabolism in AD includes decreased temporal lobe zinc levels (Wenstrup et al., *Brain Res.* 533:125–131 (1990); Constantinidis, *Encephale* 16:231–239 (1990); Corrigan et al., *Biometals* 6:149–154 (1993)), elevated (80%) cerebrospinal fluid levels (Hershey et al., *Neurology* 33:1350–1353 (1983)), increased hepatic zinc with reduced zinc bound to metallothionein (Lui et al., *J. Am. Geriatr. Soc.* 38:633–639 (1990)), a $Zn^{2+}$-modulated abnormality of APP in AD plasma (Bush et al., *Ann. Neurol.* 32:57–65 (1992)), an increase in extracellular $Zn^{2+}$-metalloproteinase activities in AD hippocampus (Backstrom et al., *J. Neurochem.* 58:983–992 (1992)), and decreased levels of astrocytic growth inhibitory factor, a metallothionein-like protein which chelates zinc (Uchida et al., *Neuron* 7:337–347 (1991)). Collectively, these reports indicate that there may be an abnormality in the uptake or distribution of zinc in the AD brain causing high extracellular concentrations and low intracellular concentrations in the brain. Meanwhile, environmentally induced elevations of brain concentrations of both zinc (Duncan et al., *J. Neurosci.* 12:1523–1537 (1992)) and aluminum (Garruto et al., *Proc. Natl. Acad. Sci. USA* 81:1875–1879 (1984); Perl et al., *Science* 217:1053–1055 (1982)) have been implicated in the pathogenesis of Guamanian amyotrophic lateral sclerosis/Parkinson's dementia complex, a disease also characterized by neurofibrillary tangles (Guiroy et al., *Proc. Natl. Acad. Sci. USA* 84:2073–2077 (1987)). Interestingly, a pervasive abnormality of zinc metabolism manifested by immunological and endocrine dysfunction has been described as a common complication of Down's syndrome (Franceschi et al., *J. Ment. Defic. Res.* 32:169–181 (1988); Bjorksten et al., *Acta. Pediatr. Scand.* 69:183–187 (1980)), a condition characterized by the invariable onset of presenile Aβ deposition and Alzheimer's disease (Rumble et al., *N. Engl. J. Med.* 320:1446–1452 (1989)).

These results indicate that abnormally high zinc concentrations increase Aβ resistance to secretase-type cleavage and also accelerate Aβ precipitation onto aluminosilicates. Zinc-induced accumulation of Aβ in the neuropil may, in turn, invoke a glial inflammatory response, free radical attack, and oxidative cross-linking to form an, ultimately, "mature" amyloid. Collectively, these findings support the biochemical rationale for the chelation approach in the therapy of Alzheimer's disease (Crapper McLachlan et al., *Lancet* 337:1304–1308 (1991)), since reduction of cerebral concentrations of both aluminum and zinc could potentially decelerate the precipitation of Aβ.

Example 5

Scatchard Analysis of $^{65}$Zn Binding to Rat Aβ$_{1-40}$

Dissolved peptides (1.2 nmol) were dot-blotted onto 0.20μ PVDF membrane (Pierce) and competition analysis performed as described in Example 1 to measure the $K_A$ of zinc binding to human Aβ$_{1-40}$ (FIG. 1).

In the present invention, rat Aβ$_{1-40}$ and human Aβ$_{1-40}$ were synthesized by solid-phase Fmoc chemistry. Purification by reverse-phase HPLC and amino acid sequencing confirmed the synthesis. The tabulated results are presented in FIG. 5. The regression line indicates a $K_A$ of 3.8 μM. Stoichiometry of binding is 1:1. Although the data points for the Scatchard curve are slightly suggestive of a biphasic curve, a biphasic iteration yields association constants of 2 and 9 μM, which does not justify an interpretation of physiologically separate binding sites.

Example 6

Effect of Zinc Upon Human, $^{125}$-human and Rat β$_{1-40}$ Aggregation Into >0.2μ Particles Stock human and rat Aβ$_{1-40}$ peptide solutions (16 μM) in water were prefiltered (Spin-X, Costar, 0.2μ cellulose acetate, 700 g), brought to 100 mM NaCl, 20 mM Tris-HCl, pH 7.4 (buffer 1)±EDTA (50 μM) or metal chloride salts, incubated (30 minutes, 37° C.) and then filtered again (700 g, 4 minutes). The fraction of the Aβ$_{1-40}$ in the filtrate was calculated by the ratio of the filtrate OD$_{214}$ (the response of the OD$_{214}$, titrated against human and rat Aβ$_{1-40}$ concentrations (up to 20 μM in the buffers used in these experiments), was determined to be linear) relative to the OD$_{214}$ of the unfiltered sample. The results are tabulated in FIG. 6. All data points are in triplicate, unless indicated. (FIG. 6a) Proportions of Aβ$_{1-40}$ incubated ±Zn$^{2+}$ (25 μM) or EDTA (50 μM) and then filtered through 0.2μ, titrated against peptide concentration. (FIG. 6b) Proportion of Aβ$_{1-40}$ (1.6 μM) filtered through 0.2μ, titrated against Zn$^{2+}$ concentration. $^{125}$I-human Aβ$_{1-40}$ ($^{125}$I-human Aβ$_{1-40}$ was prepared according to the method in J. E. Maggio, *PNAS USA* 89:5462–5466 (1992) (15,000 CPM, the kind gift of Dr. John Maggio, Harvard Medical School) was added to unlabeled Aβ$_{1-40}$ (1.6 μM) as a tracer, incubated and filtered as described above. The CPM in the filtrate and retained on the excised filter were measured by γ-counter. (FIG. 6c) Proportion of Aβ$_{1-40}$ (1.6 μM) filtered through 0.2μ following incubation with various metal ions (3 μM). The atomic number of the metal species is indicated. (FIG. 6d) Effects of Zn$^{2+}$ (25 μM) or EDTA (50 μM) upon kinetics of human Aβ$_{1-40}$ aggregation measured by 0.2μ filtration. Data points are in duplicate.

Example 7

Size Estimation of Zinc-induced Aβ Aggregates (FIGS. 7a and 7b) Proportion of β$_{1-40}$ (1.6 μM in buffer 1 (100 mM NaCl, 20 mM Tris-HCl, pH 7.4)), was incubated ±Zn$^{2+}$ (25 μM) or EDTA (50 μM) and was then filtered through filters of indicated pore sizes (Durapore filters (Ultrafree-MC, Millipore) were used for this study, hence there is a slight discrepancy between the values obtained with the 0.22μ filters in this study compared to values obtained in FIG. 2 using 0.2μ Costar filters). (FIG. 7c) $^{65}$ZnCl$_2$ (130,000 CPM, 74 nM) was used as a tracer of the assembly of the zinc-induced aggregates of human Aβ$_{1-40}$ produced in FIG. 3A. By determining the amounts of Aβ$_{1-40}$ and $^{65}$Zn in the filtrate, the quantities retarded by the filters could be determined, and the stoichiometry of the zinc: Aβ assemblies estimated. (FIG. 7d) Following this procedure, the filters, retaining Zn: Aβ assemblies, were washed with buffer 1 (100 mM NaCl, 20 mM Tris-HCl, pH 7.4)±EDTA (50 μM×300 μl, 700 g, 4 minutes). The amounts of zinc-precipitated Aβ$_{1-40}$ resolubilized in the filtrate fraction were determined by OD$_{214}$, and expressed as a percentage of the amount originally retained by the respective filters. $^{65}$Zn released into the filtrate was measured by γ-counting.

Example 8

Zinc-induced Tinctorial Amyloid Formation (FIG. 8a) depicts Zinc-induced human Aβ$_{1-40}$ precipitate stained with Congo Red. The particle diameter is 40 μ. Aβ$_{1-40}$ (200 μl×25 μM in buffer 1 (100 mM NaCl, 20 mM Tris-HCl, pH 7.4)) was incubated (30 minutes, 37° C.) in the presence of 25 μM Zn$^{2+}$. The mixture was then centrifuged (16,000 g×15 minutes), the pellet washed in buffer 1 (100 mM NaCl, 20 mM Tris-HCl, pH 7.4)±EDTA (50 μM), pelleted again and resuspended in Congo Red (1% in 50% ethanol, 5 minutes). Unbound dye was removed, the pellet washed with buffer 1 (100 mM NaCl, 20 mM Tris-HCl, pH 7.4) and mounted for microscopy. (FIG. 8b) The same aggregate visualized under polarized light, manifesting green birefringence. The experiment was repeated with EDTA (50 μM) substituted for Zn$^{2+}$ and yielded no visible material.

Example 9

Effect of Zinc and Copper Upon Human, $^{125}$I-human and Rat Aβ$_{1-40}$ Aggregation Into >0.2μ Particles Stock human and rat Aβ$_{1-40}$ peptide solutions (16 μM) in water were pre-filtered (Spin-X, Costar, 0.2μ cellulose acetate, 700 g), brought to 100 mM NaCl, 20 mM Tris-HCl, pH 7.4 (buffer 1)±EDTA (50 μM) or metal chloride salts, incubated (30 minutes, 37° C.) and then filtered again (700 g, 4 minutes). The fraction of the Aβ$_{1-40}$ in the filtrate was calculated by the ratio of the filtrate OD$_{214}$ (the response of the OD$_{214}$, titrated against human and rat Aβ$_{1-40}$ concentrations (up to 20 μM in the buffers used in these experiments), was determined to be linear) relative to the OD$_{214}$ of the unfiltered sample. All data points are in triplicate, unless indicated. (FIG. 9) A graph showing the proportions of $A\beta_{1-40}$ incubated ±$Zn^{2+}$ (25 μM) or $Cu^{2+}$ or EDTA (50 μM) and then filtered through 0.2μ, titrated against peptide concentration.

Example 10

Effect of Zinc Upon Aβ Produced in Cell Culture

A cell culture, preferably mammalian cell culture, expressing, preferably overexpressing, human APP is established according to well-known methods in the art, e.g. N. Suzuki et al., *Science* 264:1336–1340 (1994); X-D Cai et al., *Science* 259:514–516 (1993); F. S. Esch et al., *Science* 248:1122–1124 (1990). Next, zinc is added to the culture medium to final concentration from about 200 nM to about 5 μM. Then the cell cultures, containing zinc, are incubated from about 15 minutes to as long as they can survive in the culture. Preferably, the cells are incubated for 3 to 4 days. While fresh media may be added to the cultures, no spent medium should be taken out since it contains amyloid or zinc-induced Aβ aggregates.

The media which can be used are isotonic or physiological media, at physiological pH (about 7.4). Preferably Tyrode's buffer is used with calcium, magnesium, and potassium, as well as glucose. Any medium used must be devoid of cysteine, glutamate, aspartate, and histidine since these amino acids chelate zinc. Basically, any isotonic buffer or physiological medium which minimizes constituents which chelate zinc may be used. For example, Krebs Mammalian Ringer Solutions, in *Data for Biochemical Research*, 3d Edition by Dawson et al., Oxford Science Publications, pp.446 (N.Y. 1986), and page 447 for Balanced Salt Solutions, provide recipes for making various useful media. The constituents that should be left out are serum and the four amino acids mentioned above.

The cell culture should be incubated at about 37 degrees centigrade with air or $O_2/CO_2$ (the maximum concentration of $CO_2$ is 5%).

Next, the cells and the medium are harvested together. A detergent such as Triton (at concentrations of about 1–2% v:v) is added and the mixture is incubated for about 3 minutes to overnight. Preferably, however, it is incubated for about 1 to 2 hours.

After incubation, the cell debris as well as amyloid and zinc-induced Aβ aggregates are pelleted by centrifugation. The pellet is suspended in pepsin (about 2%) or in any other peptidase, and it is incubated from about 1 hour to overnight to allow digestion of the cell debris.

Again, it is pelleted, washed with PBS or any other appropriate salt solution, stained with Congo Red, washed again, pelleted to remove any unbound Congo Red, and resuspended in aqueous solution. At this point, a sample can be visually inspected under a microscope. Further, it can be quantitated using a grid.

Example 11

Assay for Predicting the Effectiveness of Candidate Reagents in Cell Culture The assay is set up in duplicate as described in Example 10. However, a candidate reagent is added to one of the two cell cultures and EDTA is added to the other cell culture. After the final step in Example 10, the amount of amyloid and zinc-induced Aβ aggregates are compared under the microscope. The probability and level of effectiveness of the candidate reagent is assessed based on the degree decrease in formation of amyloid and zinc-induced Aβ aggregates in the cell culture.

Example 12

Rapid Assay for Detection of $A\beta_{1-40}$ Amyloid Formation in Biological Fluid Cerebrospinal fluid (CSF) is obtained from a healthy human subject (control) and a human patient suspected of amyloidosis. Both samples of CSF are titrated by serial dilutions, e.g., neat, 1:2, 1:4, 1:6, . . . ; dilutions may be made up to 1:10,000.

To each of the samples, an equal amount of Aβ peptide in water is added to the final concentration of above about 10 μM, preferably about 10 to about 25 μM.

Next, a solution which contains a heavy metal cation capable of binding to a peptide comprising at least amino acids 6 to 28 of Aβ, preferably $Zn^{2+}$, plus NaCl and a buffer, e.g., Tris at pH 7.4, is added to the final heavy metal cation, e.g., $Zn^{2+}$, to a final concentration of about above 300 nM, preferably 25 μM.

Then, the samples are centrifuged to form pellets. Pellets are stained with an amyloid-staining dye, e.g., Congo Red, and observed under a microscope, thereby comparing levels of Aβ amyloid in the control versus the sample from the patient with amyloidosis. If quantification of amyloid is desired, a grid can be used.

Example 13

Rapid Assay for Detection of Aβ amyloid formation in biological fluid using $^3H$-Aβ

The assay is set up as explained in Example 12, except that the Aβ peptide added is labelled beforehand by tritium. Moreover, after centrifugation, the pellets are counted in a scintillation counter.

The preferred method of detecting the amyloid, however, is by using filtration techniques as described above instead of centrifugation. After the samples are passed through a filter, the filters are added to scintillation fluid and the counts are determined.

Comparing the CPM from control samples with samples of the suspected amyloidosis patient, it can be determined whether the patient is in fact afflicted with amyloidosis. That is, an elevated CPM count in the patient samples compared to the control samples is indicative of amyloidosis.

Having now fully described this invention, it will be understood by those of skill in the art that it can be performed within any wide range of equivalent modes of operation as well as other parameters without affecting the scope of the invention or any embodiment thereof.

All patents and publications cited in the present specification are incorporated by reference herein in their entirety.

What is claimed is:

1. A rapid analytical method for detection of Aβ amyloid formation in a biological fluid from a human patient suspected of amyloidosis by comparing with Aβ amyloid formation in a biological fluid from a control human subject which comprises:

(a) preparing a first set of reaction mixtures comprising neat biological fluid from the control human subject, and serial dilutions of said fluid from the control subject made in aqueous buffer or physiological solution;

(b) preparing a second set of reaction mixtures comprising the same type of neat biological fluid from the human patient suspected of amyloidosis, and serial dilutions of said fluid from the patient made in aqueous buffer or physiological solution;

(c) adding an equal amount of Aβ peptide comprising at least amino acids 6 to 28 of Aβ to each serial dilution sample and each neat sample;

(d) contacting each of the first and the second set of reaction mixtures with an amount greater than 300 nM but less than or equal to 50 μM of an added heavy metal cation capable of binding to an Aβ peptide comprising at least amino acids 6 to 28 of Aβ;

(e) centrifuging each of the first and the second sets of reaction mixtures to give a first and a second set of pellets, respectively; and (f) measuring and comparing the amount of amyloid in the first and the second set of pellets and thereby detecting Aβ amyloid formation in the biological fluid from the human patient suspected of amyloidosis.

2. A rapid analytical method for detection of Aβ amyloid formation in a biological fluid as claimed in claim 1, wherein said biological fluid is cerebrospinal fluid.

3. A rapid analytical method for detection of Aβ amyloid formation in a biological fluid as claimed in claim 2, wherein in (d), said heavy metal cation capable of binding to an Aβ peptide comprising at least amino acids 6 to 28 of Aβ is zinc.

4. A rapid analytical method for detection of Aβ amyloid formation in a biological fluid as claimed in claim 1, wherein the contacting each of the first and the second set of reaction mixtures is with an amount greater than 300 nM but equal to or less than 25 μM of an added heavy metal cation capable of binding to an Aβ peptide comprising at least amino acids 6 to 28 of Aβ.

* * * * *